(12) United States Patent
Saar et al.

(10) Patent No.: US 11,523,923 B2
(45) Date of Patent: *Dec. 13, 2022

(54) COMPACT CRIMPING DEVICE

(71) Applicant: Edwards Lifesciences Corporation, Irvine, CA (US)

(72) Inventors: Tomer Saar, Pardes Hanna-Karkur (IL); Gregory Rinberg, Haifa (IL)

(73) Assignee: Edwards Lifesciences Corporation, Irvine, CA (US)

(*) Notice: Subject to any disclaimer, the term of this patent is extended or adjusted under 35 U.S.C. 154(b) by 230 days.

This patent is subject to a terminal disclaimer.

(21) Appl. No.: 17/247,605

(22) Filed: Dec. 17, 2020

(65) Prior Publication Data

US 2021/0106446 A1 Apr. 15, 2021

Related U.S. Application Data

(63) Continuation of application No. 16/935,044, filed on Jul. 21, 2020, which is a continuation of application (Continued)

(51) Int. Cl.
*A61F 2/95* (2013.01)
*A61F 2/24* (2006.01)

(52) U.S. Cl.
CPC .............. *A61F 2/95* (2013.01); *A61F 2/9524* (2020.05); *A61F 2/2412* (2013.01);
(Continued)

(58) Field of Classification Search
CPC .. A61F 2/2433; A61F 2/95; A61F 2002/9522; A61F 2002/9583;
(Continued)

(56) References Cited

U.S. PATENT DOCUMENTS 1,438,681 A 12/1922 Bath
1,493,515 A 5/1924 Berthold
(Continued)

FOREIGN PATENT DOCUMENTS

CN 101257863 A 9/2008
CN 102762170 A 10/2012
(Continued)

OTHER PUBLICATIONS http://www.machinesolutions.org/custom.sub.-tools.sub.--equipment/HV200.h- tm, 2 pages, Aug. 22, 2006.
(Continued)

*Primary Examiner* — Lee D Wilson
*Assistant Examiner* — Aaron R McConnell
(74) *Attorney, Agent, or Firm* — Klarquist Sparkman, LLP

(57) ABSTRACT

Disclosed herein is a method of crimping a prosthetic heart valve using a compact crimping mechanism. The crimping mechanism includes a plurality of jaws configured for coordinated inward movement toward a crimping axis to reduce the size of a crimping iris around a stented valve. A rotating cam wheel acts on the jaws and displaces them inward. An actuation mechanism includes a lead screw, carriage assembly and a linkage to rotate the cam wheel with significant torque.

19 Claims, 16 Drawing Sheets

Related U.S. Application Data

No. 15/630,711, filed on Jun. 22, 2017, now Pat. No. 10,716,691.

(60) Provisional application No. 62/354,551, filed on Jun. 24, 2016.

(52) U.S. Cl.
CPC ........... *A61F 2/2427* (2013.01); *A61F 2/2433* (2013.01); *A61F 2/9522* (2020.05)

(58) Field of Classification Search
CPC . B65D 45/32; B65D 45/322; Y10T 29/49925; Y10T 29/53987; Y10T 29/53996
USPC ..................... 29/235, 237, 237.5, 238, 283.5
See application file for complete search history.

(56) References Cited

U.S. PATENT DOCUMENTS

| | | |
|---|---|---|
| 2,079,498 A | 5/1937 | Douglas |
| 2,664,996 A | 1/1954 | Andrews |
| 2,787,925 A | 4/1957 | Buchanan et al. |
| 2,974,367 A | 3/1961 | Doering et al. |
| 3,154,978 A | 11/1964 | Baker |
| 3,307,451 A | 3/1967 | Schuetz |
| 3,417,598 A | 12/1968 | Valente |
| 3,695,087 A | 10/1972 | Tuberman |
| 4,308,744 A | 1/1982 | Baker |
| 4,350,036 A | 9/1982 | Valente |
| 4,454,657 A | 6/1984 | Yasumi |
| 4,578,982 A | 4/1986 | Schrock |
| 5,261,263 A | 11/1993 | Whitesell |
| 5,411,521 A | 5/1995 | Putnam et al. |
| 5,437,083 A | 8/1995 | Williams et al. |
| 5,626,604 A | 5/1997 | Cottone, Jr. |
| 5,749,921 A | 5/1998 | Lenker et al. |
| 5,810,873 A | 9/1998 | Morales |
| 5,836,952 A | 11/1998 | Davis et al. |
| 5,893,852 A | 4/1999 | Morales |
| 5,913,871 A | 6/1999 | Werneth et al. |
| 5,918,511 A | 7/1999 | Sabbaghian et al. |
| 5,951,540 A | 9/1999 | Verbeek |
| 5,992,000 A | 11/1999 | Humphrey et al. |
| 6,007,543 A | 12/1999 | Ellis et al. |
| 6,009,614 A | 1/2000 | Morales |
| 6,051,002 A | 4/2000 | Morales |
| 6,074,381 A | 6/2000 | Dinh et al. |
| 6,082,990 A | 7/2000 | Jackson et al. |
| 6,125,523 A | 10/2000 | Brown et al. |
| 6,167,605 B1 | 1/2001 | Morales |
| 6,176,116 B1 | 1/2001 | Wilhelm et al. |
| 6,309,383 B1 | 10/2001 | Campbell et al. |
| 6,352,547 B1 | 3/2002 | Brown et al. |
| 6,360,577 B2 | 3/2002 | Austin |
| 6,364,870 B1 | 4/2002 | Pinchasik |
| 6,387,117 B1 | 5/2002 | Arnold, Jr. et al. |
| 6,558,418 B2 | 5/2003 | Carpentier et al. |
| 6,618,921 B1 | 9/2003 | Thornton |
| 6,629,350 B2 | 10/2003 | Motsenbocker |
| 6,651,478 B1 | 11/2003 | Kokish |
| 6,682,553 B1 | 1/2004 | Webler, Jr. |
| 6,730,118 B2 | 5/2004 | Spenser et al. |
| 6,769,161 B2 | 8/2004 | Brown et al. |
| 6,823,576 B2 | 11/2004 | Austin |
| 6,840,081 B2 | 1/2005 | Kokish |
| 6,889,579 B1 | 5/2005 | Brown |
| 6,915,560 B2 | 7/2005 | Austin |
| 6,920,674 B2 | 7/2005 | Thornton |
| 6,925,847 B2 | 8/2005 | Motsenbocker |
| 6,931,899 B2 | 8/2005 | Goff et al. |
| 6,968,607 B2 | 11/2005 | Motsenbocker |
| 6,988,881 B2 | 1/2006 | Motsenbocker et al. |
| 7,010,953 B2 | 3/2006 | Stupecky |
| 7,021,114 B2 | 4/2006 | Perreault |
| 7,069,794 B2 | 7/2006 | Motsenbocker et al. |
| 7,096,554 B2 | 8/2006 | Austin et al. |
| 7,143,625 B2 | 12/2006 | Edin |
| 7,152,452 B2 | 12/2006 | Kokish |
| 7,207,204 B2 | 4/2007 | Weber et al. |
| 7,225,518 B2 | 6/2007 | Eidenschink et al. |
| 7,284,401 B2 | 10/2007 | Larson et al. |
| 7,389,670 B1 | 6/2008 | Kokish et al. |
| 7,415,861 B2 | 8/2008 | Sokel |
| 7,487,579 B2 | 2/2009 | Eidenschink et al. |
| 7,530,253 B2 | 5/2009 | Spenser et al. |
| 7,587,801 B2 | 9/2009 | Austin |
| 7,628,051 B1 | 12/2009 | Kokish et al. |
| 7,892,201 B1 | 2/2011 | Laguna et al. |
| 7,895,876 B2 | 3/2011 | Spenser et al. |
| 7,967,138 B2 | 6/2011 | Ryan et al. |
| 8,006,535 B2 | 8/2011 | Righini et al. |
| 8,112,857 B2 | 2/2012 | Voelkl |
| 8,312,614 B2 | 11/2012 | Sokel |
| 2003/0192164 A1 | 10/2003 | Austin |
| 2006/0213049 A1 | 9/2006 | Serrano et al. |
| 2007/0056346 A1 | 3/2007 | Spenser et al. |
| 2007/0061009 A1 | 3/2007 | Spenser et al. |
| 2009/0043249 A1 | 2/2009 | Sokel |
| 2010/0292780 A1 | 11/2010 | Straubinger et al. |
| 2012/0239142 A1 | 9/2012 | Liu et al. |

FOREIGN PATENT DOCUMENTS

| | | |
|---|---|---|
| DE | 9034 C | 3/1880 |
| EP | 1656908 A1 | 5/2006 |
| WO | 201994014573 A1 | 7/1994 |
| WO | 0121103 A2 | 3/2001 |
| WO | 03047468 A1 | 6/2003 |

OTHER PUBLICATIONS http://www.machinesolutions.org/custom.sub.-tools.sub.--equipment/HV200.s- ub.--specs.htm, 1 page, Aug. 22, 2006.

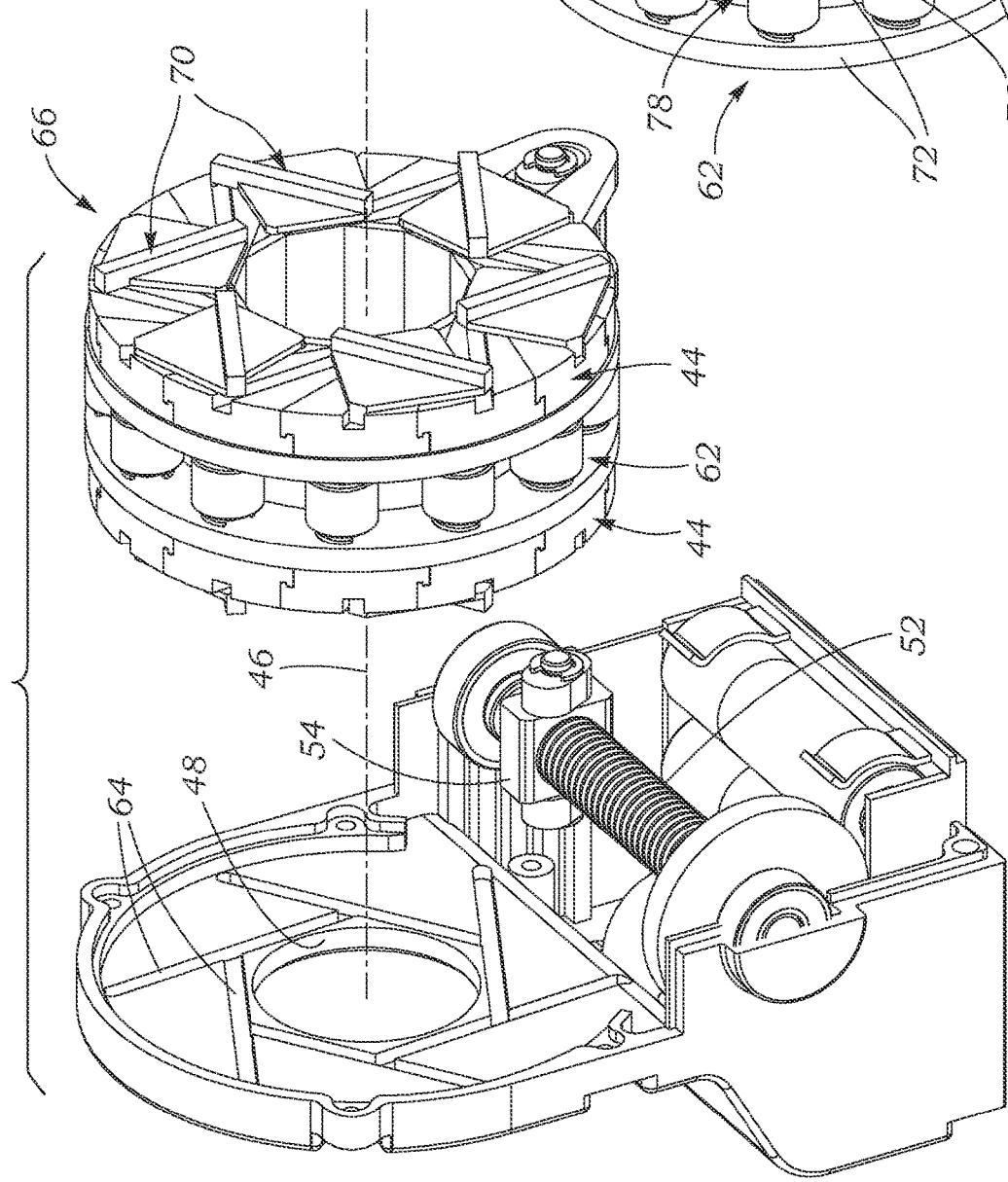
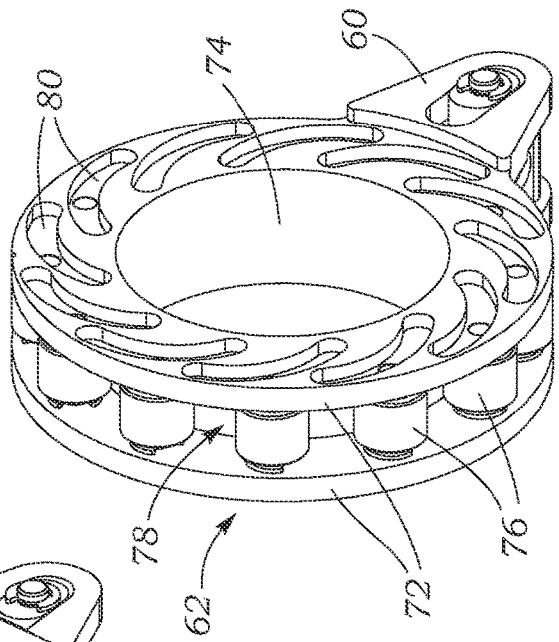

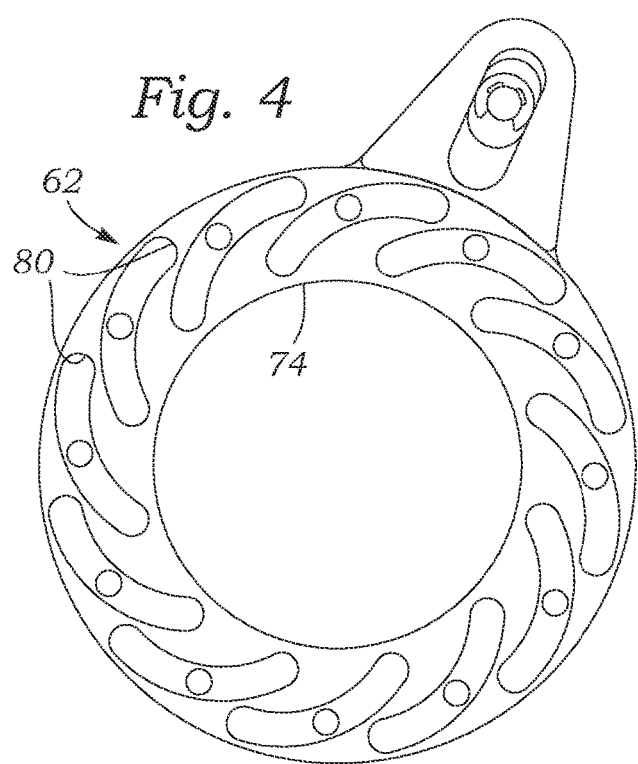
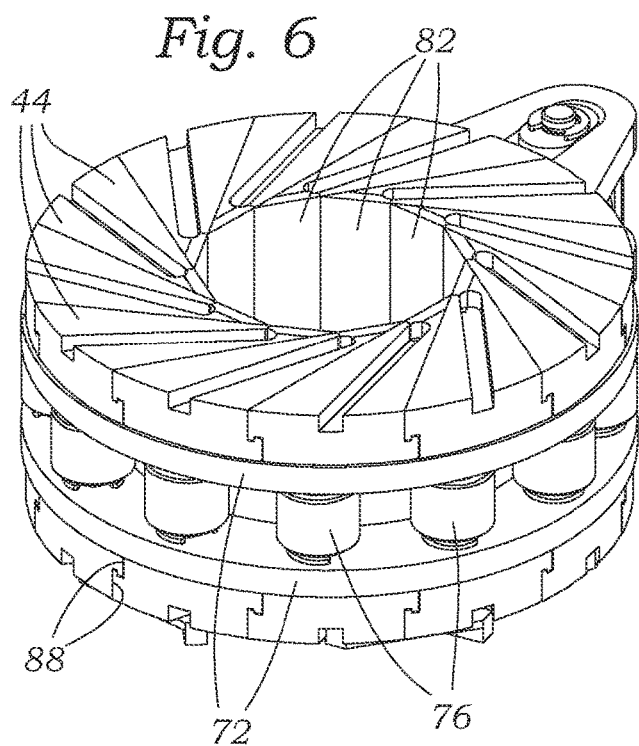
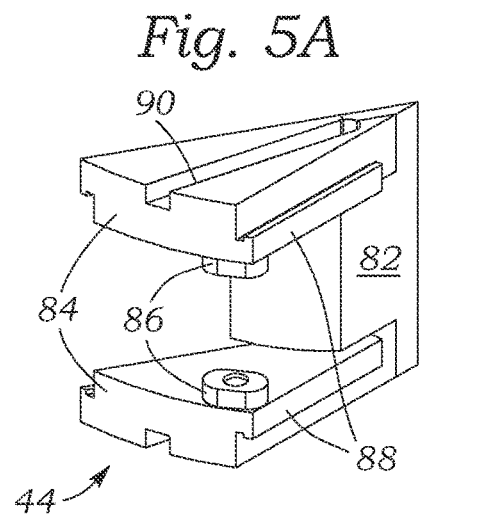
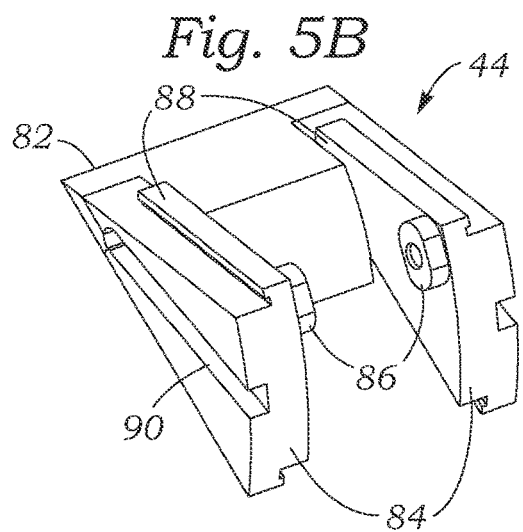
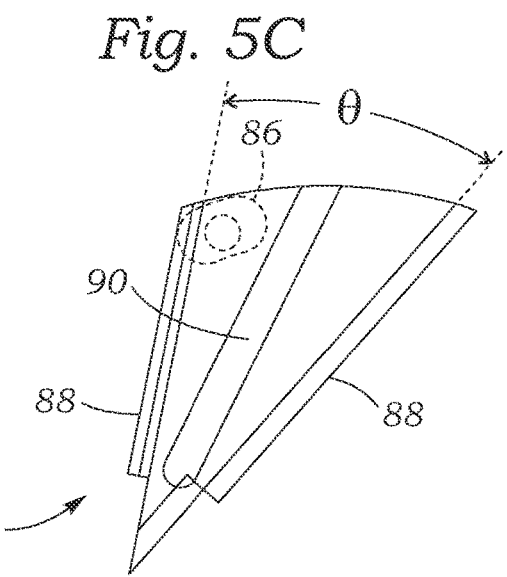

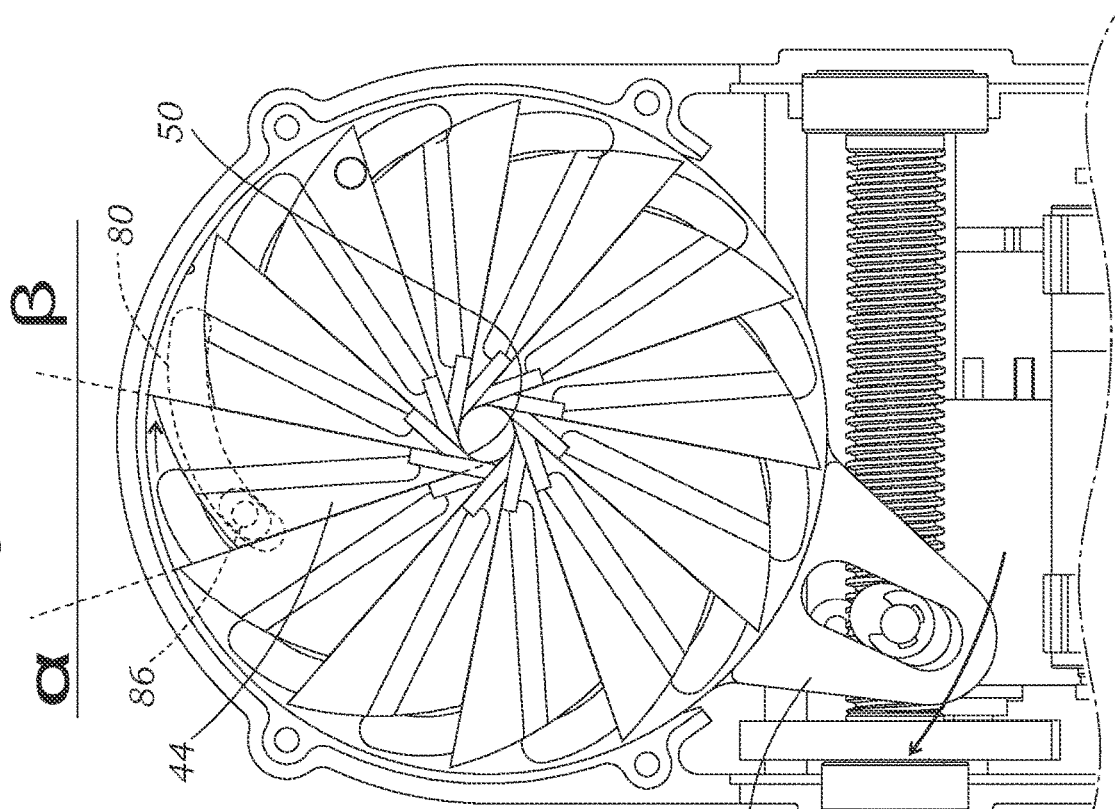
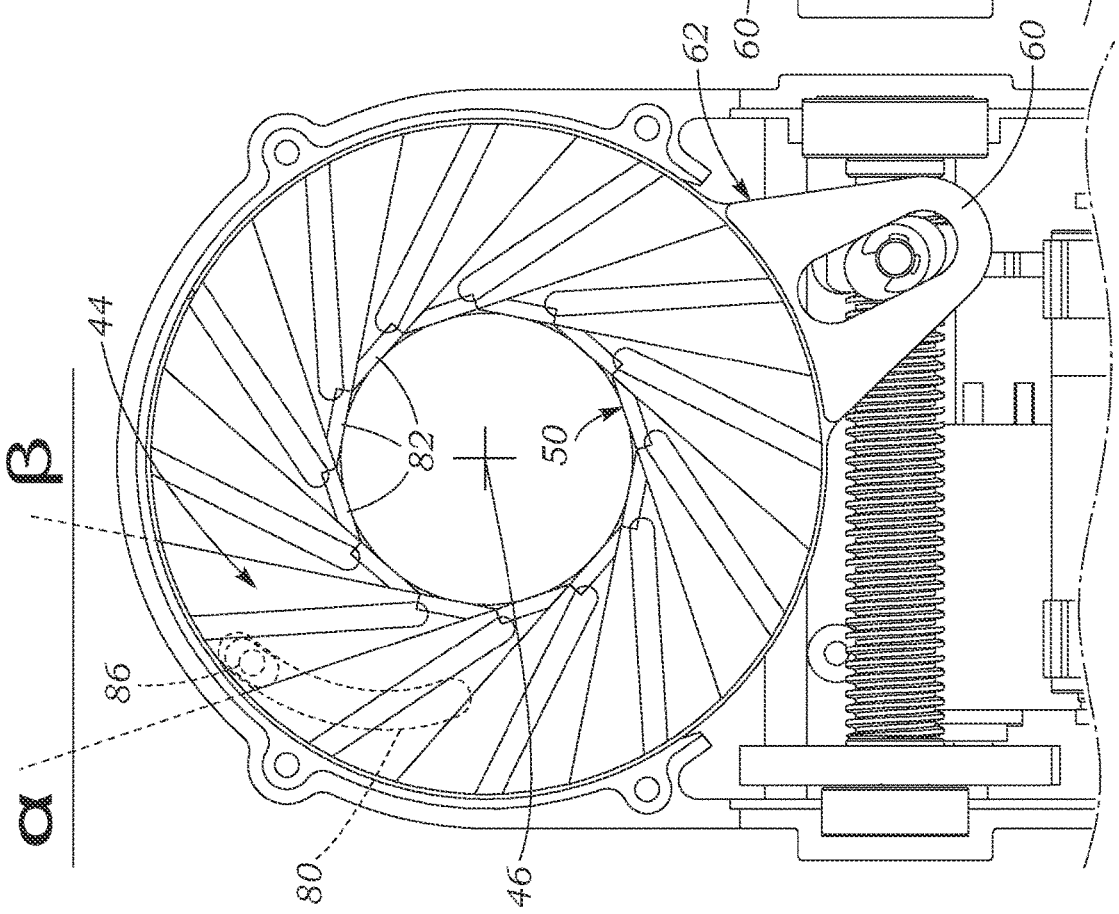

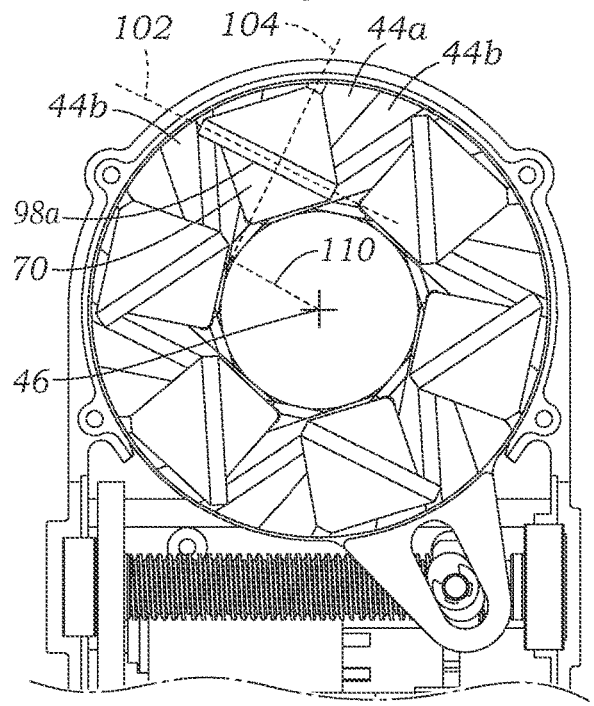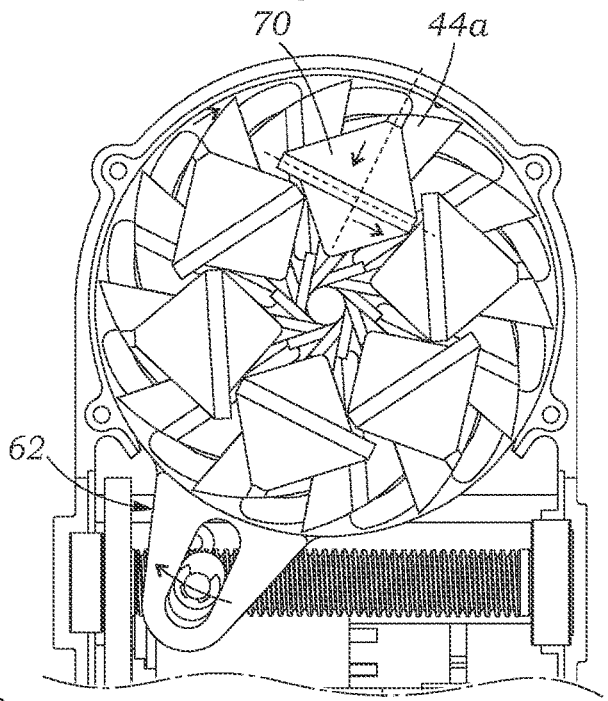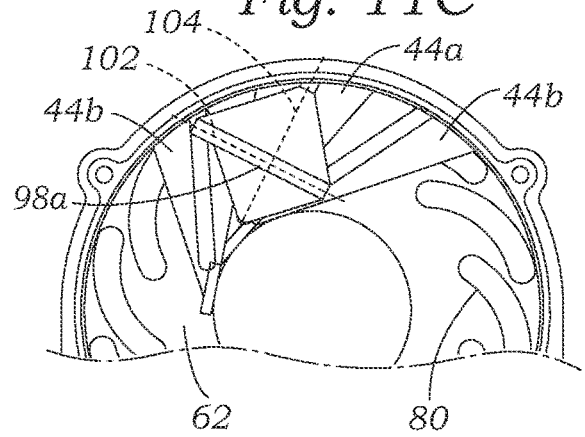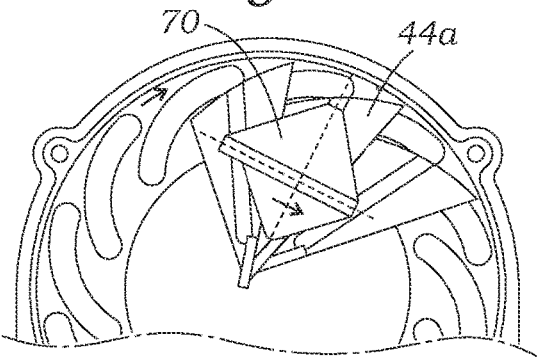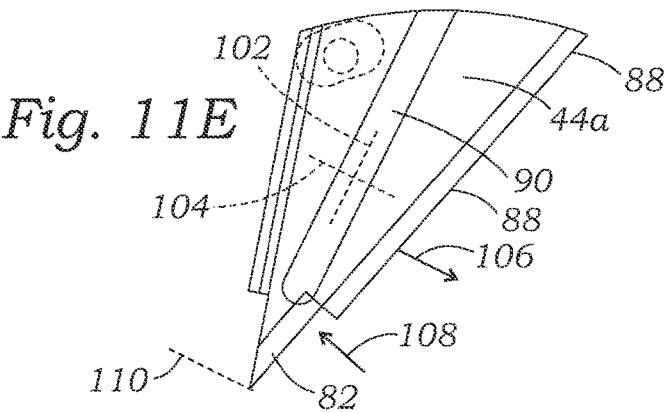

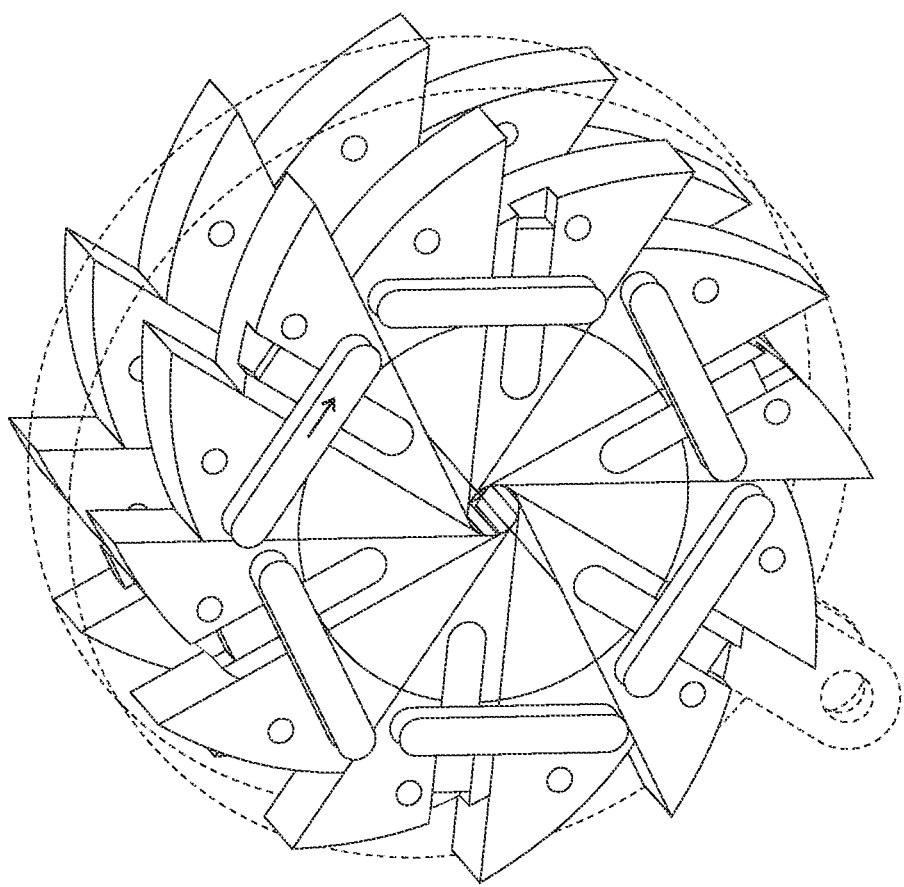
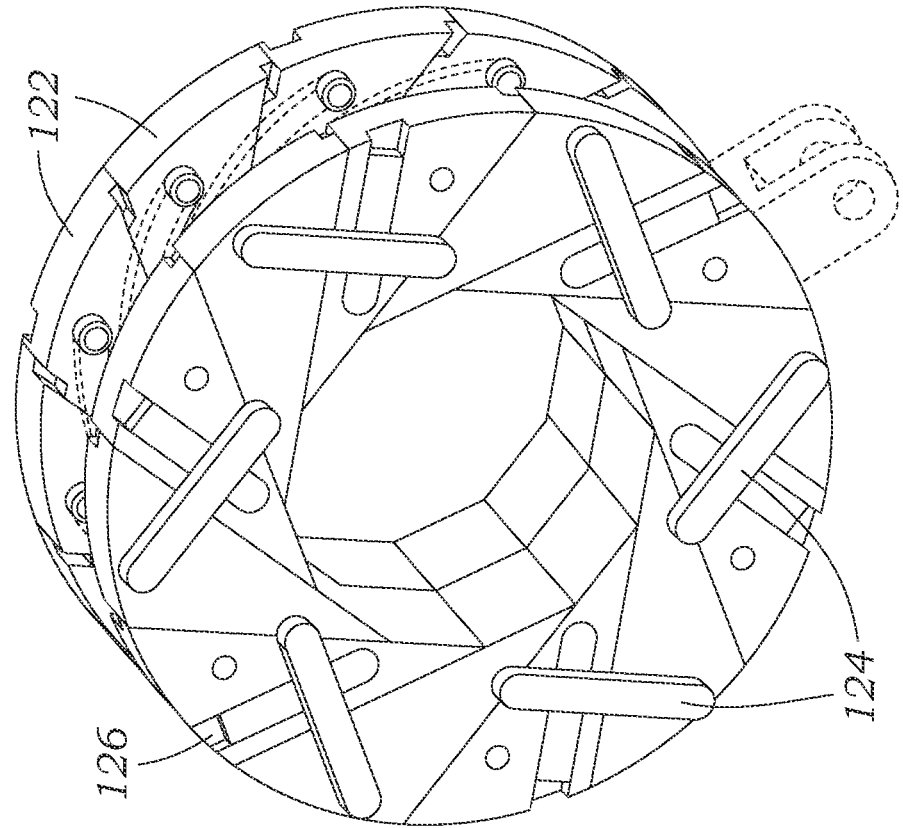
Fig. 12A
Fig. 12B

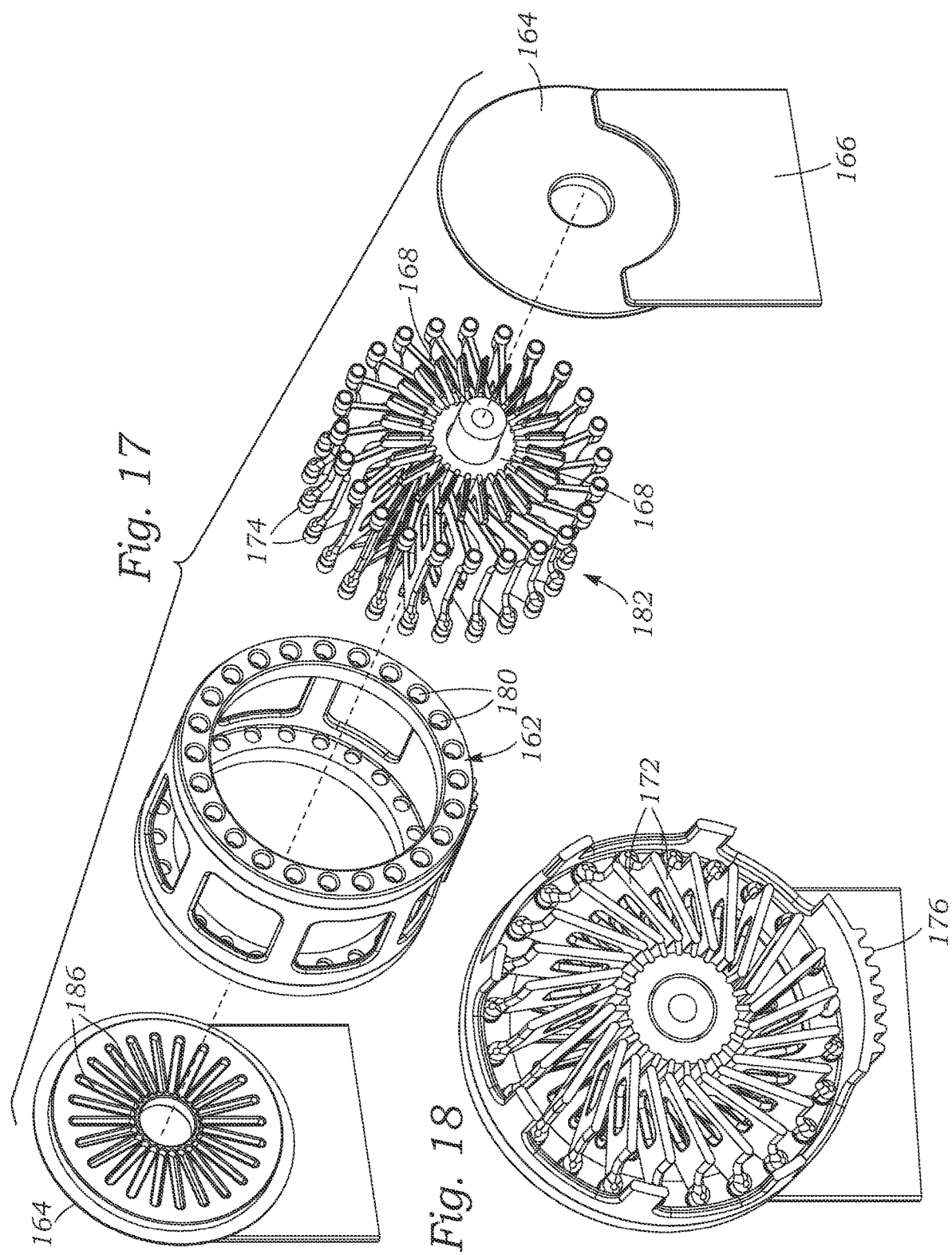

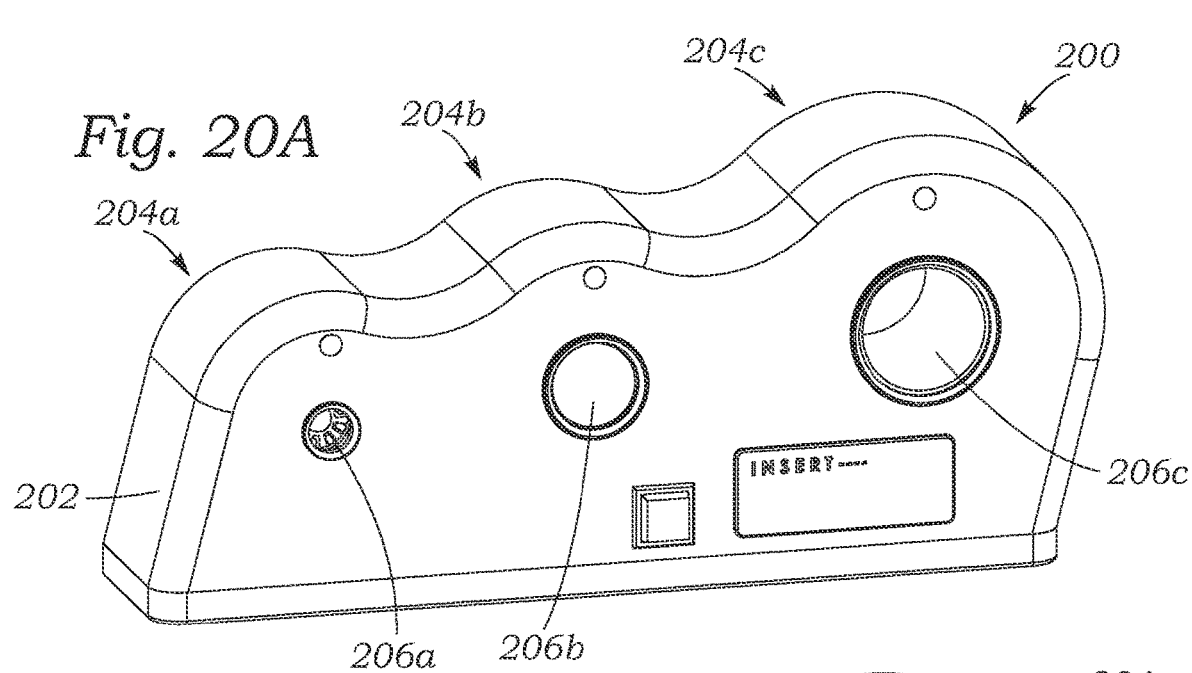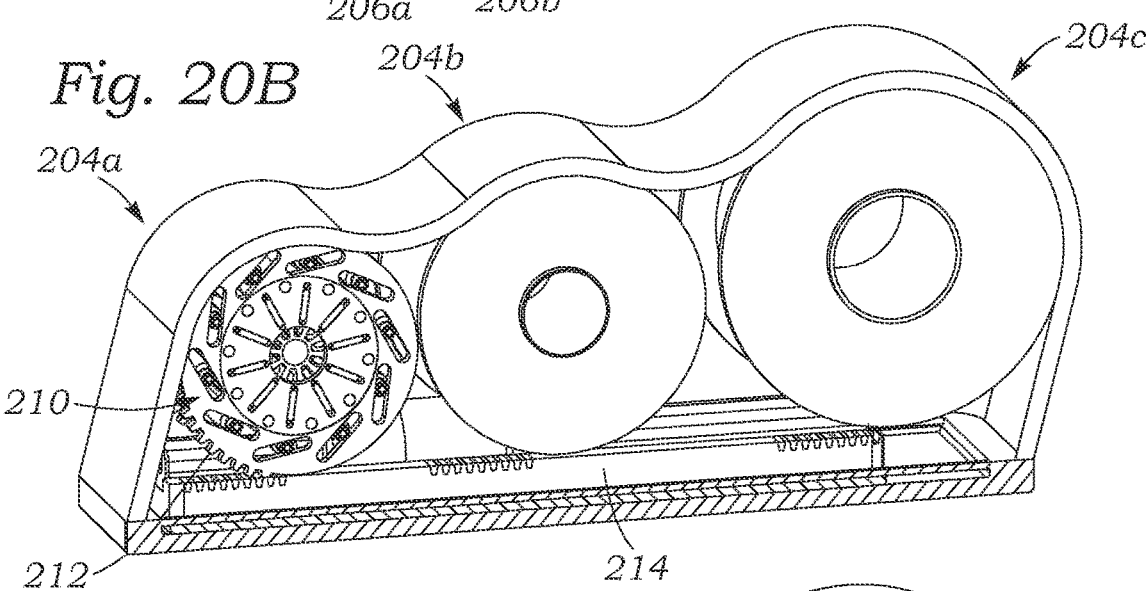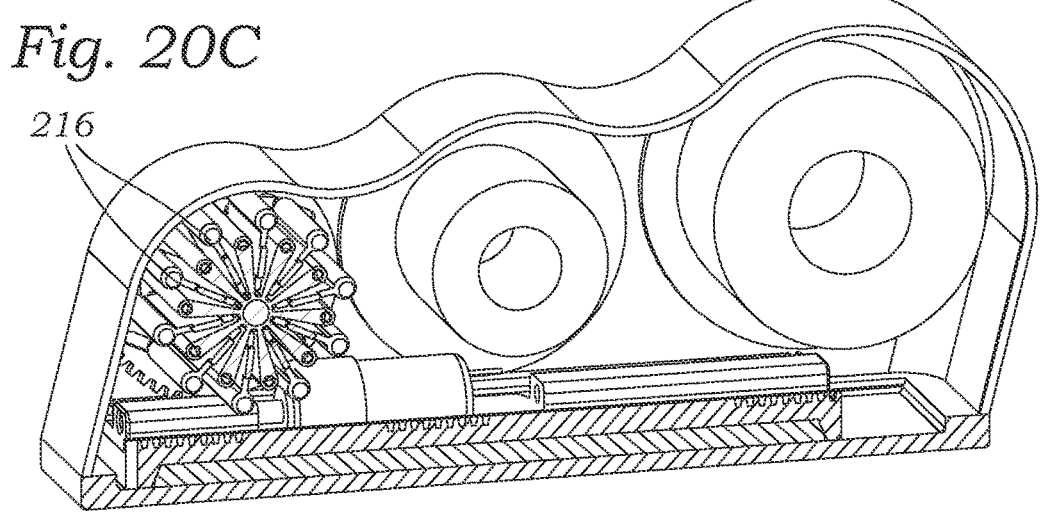

COMPACT CRIMPING DEVICE

CROSS-REFERENCE TO RELATED APPLICATIONS

The present application is a continuation of U.S. application Ser. No. 16/935,044, filed Jul. 21, 2020, which is a continuation of U.S. application Ser. No. 15/630,711, filed Jun. 22, 2017, now issued as U.S. Pat. No. 10,716,691, which claims priority under 35 U.S.C. § 119 to U.S. Provisional Application No. 62/354,551, filed Jun. 24, 2016, each of which is incorporated herein by reference in its entirety.

FIELD OF THE INVENTION

The present invention relates to a crimping device and, more particularly, to a compact device for crimping devices, such as a stented prosthetic valve such as a heart valve, from a large diameter to a smaller diameter.

BACKGROUND OF THE INVENTION

A stent is a generally cylindrical prosthesis introduced into a lumen of a body vessel via a catheterization technique. Stents may be self-expanding or balloon expandable. Balloon-expandable stents are typically crimped from an initial large diameter to a smaller diameter prior to advancement to a treatment site in the body. Before crimping, a balloon expandable stent is typically placed over an expandable balloon on a catheter shaft. In cases where the stent was manufactured in its fully crimped diameter, the stent is expanded and then crimped on the balloon. To ensure safety, the crimping process should be performed in a sterile environment. Over the years, attempts have been made to crimp the stent on a balloon during the operation in the sterile field. However, most stents are now "pre-crimped" on a suitable balloon in the factory and then delivered to the physician ready for use.

One example of a crimping device for stents based on movable jaws is disclosed in U.S. Pat. No. 6,360,577 to Austin. This crimping device uses sloped planes which force jaws to move from an open position to a closed position. One primary shortcoming is that the length of the sloped plane is given by a whole circle (360°) divided by the number of activated jaws. A long-sloped plane is preferable to reduce circumferential resistance or friction forces, but in order to achieve a smooth aperture for crimping the stent a large number of jaws is needed, which means a shorter sloped plane, less leverage and higher frictional forces. Therefore, the effectiveness of this type of device is substantially limited and may only be practical for stents which have a diameter of 1.5 to 4.0 mm in their expanded size.

In recent years, a variety of prosthetic valves have been developed wherein a valve structure is mounted on a stent and then delivered to a treatment site via a percutaneous catheterization technique. Prosthetic valves are typically much larger in diameter relative to coronary stents. While a typical expanded coronary stent diameter is only 1.5 to 4.0 mm, a stented prosthetic valve diameter will typically be in the range of about 19 to 29 mm, at least 5 times larger.

In another difference, coronary stents are stand-alone metallic devices which may be crimped over a balloon prior to packaging. For prosthetic valves, the stent functions as a scaffold to hold a valve structure which is typically made of biological materials such as pericardium valves or harvested valves. For improved function after deployment, it is often desirable to package such valves in the open (i.e., expanded) state in a preserving solution. Consequently, it is necessary to crimp the valve in the operation room a few minutes before implantation, therefore precluding pre-crimping by the manufacturer over a balloon.

Due to the unique crimping requirements for stent-based prosthetic valves, it has been found that existing crimping devices configured for use with coronary stents are not suitable for use stent-based prosthetic valves. In addition, as discussed above, existing crimping mechanisms suffer from a variety of shortcomings which limit their ability to be adapted for use with stent-based prosthetic valves. Due to the deficiencies associated with existing crimping technology, a new crimping device was described in co-owned U.S. Pat. No. 6,730,118 to Spenser, et al. and relates to a crimping device that is adapted to crimp a prosthetic valve as part of the implantation procedure.

Another version of a prosthetic heart valve crimper is marketed by Machine Solutions Inc. of Flagstaff, Ariz. The HV200 is a disposable crimper that uses multiple pivoting segments to crimp percutaneous heart valves. The Machine Solutions crimpers are also disclosed in U.S. Pat. Nos. 6,629,350 and 6,925,847, both to Motsenbocker. These crimping devices are based on segments which rotate about pivot pins to create radial compression. Unfortunately, the pivoting design tends to concentrate stress in certain areas of the individual segments, and in the mechanism for pivoting them. Also, the user must apply significant force to close the crimper aperture around a relatively large percutaneous heart valve.

U.S. Pat. No. 7,530,253 discloses a crimping mechanism for prosthetic heart valves having linearly moving jaws which has the capacity to crimp a relatively large size valve down to a small delivery size, but is also relatively large in size.

Although the heart valve crimping technology available to date provides an improvement over the existing stent crimper technology, it has been found that a need still exists for a more effective device. It is desirable that such a device be capable of crimping a valve from a diameter of about 29 mm to a crimped size of about 6 mm without requiring excessive force and without inducing high mechanical stresses within the device. It is also desirable that such a device is simple to use and relatively inexpensive to manufacture. It is also desirable that such a device be sterile and suitable for manual operation in a catheter lab or operating room. The present invention addresses this need.

SUMMARY OF THE INVENTION

The present invention provides a method and apparatus for crimping expandable prosthetic heart valves having support frames and stents. The crimping mechanism includes a plurality of jaws configured for coordinated inward movement toward a crimping axis to reduce the size of a crimping iris around a stented valve. A rotating cam wheel acts on the jaws and displaces them inward. A number of Cartesian guide elements cooperate with the jaws to distribute forces within the crimping mechanism. The guide elements are located between the crimping jaws and an outer housing and are constrained by the outer housing for movement along lines that are tangential to a circle centered on the crimping axis. The guide elements engage at least some of the crimping jaws while the rest are in meshing engagement so as to move in synch. An actuation mechanism includes a lead screw, carriage assembly and a linkage to rotate the cam wheel with significant torque.

In one embodiment, a prosthetic valve crimping device capable of reducing the diameter of an expandable prosthetic stented valve comprises a plurality of crimping jaws in meshing engagement and circumferentially arranged around a crimping orifice having a central crimping axis, each having inner crimping wedges. A rotating cam wheel acts on the crimping jaws and displaces them generally radially inward, while a stationary outer housing contains the cam wheel and crimping jaws. Finally, a plurality of guide elements are each constrained by fixed grooves in the outer housing for movement between first and second positions along lines that are tangential to a circle around the central axis, wherein the guide elements move at least some of the crimping jaws along the lines such that all of the crimping wedges of the crimping jaws translate inward along radial lines toward the crimping axis.

In one aspect, the crimping wedges are made of a different material than the rest of the crimping jaws. The guide elements may be separate elements from the crimping jaws. Preferably, the guide elements are rigidly coupled to the at least some of the crimping jaws by being integrally formed therewith or fastened thereto.

Advantageously, the crimping jaws each comprise an assembly of a pair of traveling blocks flanking the cam wheel and one of the crimping wedges that extends across a central orifice in the cam wheel. The cam wheel may include two disks having spiral cam slots that act on cams secured to each of the flanking traveling and that extend axially inward into the cam slots. Also, the cam wheel disks may each have a cam lever projecting radially outward therefrom that is driven by a carriage assembly on a lead screw. Preferably, a linkage between the cam levers and the carriage assembly increases a torque applied to the cam wheel when the carriage assembly reaches opposite ends of the lead screw.

In a second aspect, the present application discloses a prosthetic valve crimping device capable of reducing the diameter of an expandable prosthetic stented valve. The device has a plurality of crimping jaws in meshing engagement and circumferentially arranged around a crimping orifice having a central crimping axis, wherein the crimping jaws each comprise an assembly of a pair of spaced apart traveling blocks and a radially inner crimping wedge that extends therebetween. A rotating cam wheel acts on the crimping jaws and displaces them generally radially inward, the cam wheel including two disks having spiral cam slots that act on cams secured to each of the flanking traveling blocks and that extend axially inward into the cam slots. A stationary outer housing contains the cam wheel and crimping jaws, and a lower actuation mechanism including a lead screw and carriage assembly is coupled to rotate the cam wheel. The pair of traveling blocks of at least some of the crimping jaws are constrained by fixed grooves in the outer housing for movement along lines that are tangential to a circle around the central axis such that all of the crimping wedges of the crimping jaws translate inward along radial lines toward the crimping axis.

In the device of the second aspect, the cam wheel disks each may have a cam lever projecting radially outward therefrom that is driven by the carriage assembly on the lead screw via a linkage between the cam levers and the carriage assembly that increases a torque applied to the cam wheel when the carriage assembly reaches opposite ends of the lead screw. Further, a drive motor may be provided to actuate the lead screw. Also, the crimping wedges may be made of a different material than the rest of the crimping jaws.

The device of the second aspect may further include a plurality of guide elements which are each constrained by fixed grooves in the outer housing for movement between first and second positions along lines that are tangential to a circle around the central axis, the guide elements moving at least some of the crimping jaws along the lines such that all of the crimping wedges of the crimping jaws translate inward along radial lines toward the crimping axis.

In one embodiment, there are half the number of guide elements as crimping jaws, such that some of the crimping jaws are driven and some are followers. Preferably, the guide elements are rigidly connected to the traveling blocks of half of the crimping jaws by being integrally formed therewith or fastened thereto.

In either aspect, each of the guide elements may comprise a rectilinear plate in an irregular diamond shape with four vertices and straight sides therebetween with an indentation on one side adjacent one of the vertices, and when the guide elements are displaced to the second positions along the lines, one of the vertices of each fits closely within the indentation on the adjacent guide member, and the nested contact between all of the guide elements in this manner provides a positive stop on further inward movement of the crimping mechanism.

BRIEF DESCRIPTION OF THE DRAWINGS

FIG. 3B is a partially exploded perspective view of the exemplary crimping mechanism with a movable crimping jaw combination assembled, while FIG. 3C is a perspective view of an exemplary cam wheel that forms a part of the crimping jaw combination;

FIG. 4 is an elevational view of the central cam wheel that forms a part of the movable crimping jaw combination;

FIGS. 5A and 5B are different perspectives of one of the crimping jaws showing inner cam followers, and FIG. 5C is an elevational view;

FIG. 6 is a perspective view of the movable crimping jaw combination including the cam wheel, crimping jaws, and a plurality of Cartesian guide elements;

FIGS. 7A and 7B are elevational views of the inner crimping mechanism showing the central cam wheel and crimping jaws assembled thereon in both open and closed crimping jaw positions;

FIG. 9A is a view of a plurality of the Cartesian guide elements arranged in space in the same manner as they would be when interacting with the outer housing of the crimping mechanism of FIG. 8, while

FIGS. 11A and 11B are elevational views similar to FIGS. 7A and 7B and also showing guide elements interacting with the crimping jaws;

FIGS. 11C and 11D are partial cutaways of FIGS. 11A and 11B showing the interaction of just one of the guide elements and three of the crimping jaws;

FIG. 11E isolates a central one of the crimping jaws from FIGS. 11C and 11D to show its relative and absolute movements;

FIGS. 12A and 12B are schematic perspective views of an alternative embodiment of a crimping mechanism of the present application in both open and closed crimping jaw positions, much like that of FIGS. 1A-11E but with modified guide elements;

FIG. 17 is an exploded view of the crimping mechanism with a compressible jaw;

FIG. 18 is a cutaway perspective view of the crimping mechanism with a compressible jaw;

FIGS. 20A-20C are perspective and cutaway views of a series of progressively sized crimping mechanisms each with a compressible jaw;

FIG. 22A is a perspective view of an alternative crimping mechanism having a modified actuating mechanism and an outer housing shown in phantom, while

DETAILED DESCRIPTION OF THE PREFERRED EMBODIMENTS

The present invention provides an improved crimper for stents or prosthetic valves. The particularly advantageous features of the present crimper enable reduction in diameter of relatively large stents or prosthetic valves in conjunction with a small sized crimper that generates high crimping forces to result in small final diameters. The crimper is especially suited for crimping prosthetic heart valves which have expanded diameters significantly larger than most stents currently in use. According to Chessa, et al., the Palmaz-Genesis XD stents (Cordis J&J Interventional Systems Co.) are designed for an expansion range of 10-18 mm, and are considered as either large or extra-large stents (see, Results and Mid-long-term Follow-up of Stent Implantation for Native and Recurrent Coarctation of the Aorta, European Heart Journal Volume 26, No. 24, Pp. 2728-2732, published online Sep. 26, 2005). The most frequently used stents are significantly smaller, in the 3-6 mm range. Crimpers for these stents have proved inadequate for reducing in size even larger prosthetic valves, such as the stented prosthetic heart valves. Conversely, aspects of the present crimper may be applicable for use in crimping stents as well, although certain features described herein make it particularly well-suited for crimping large diameter stents, stent grafts, and prosthetic valves.

The term "stented valve" as used herein refers to prosthetic valves for implant, primarily prosthetic heart valves but also conceivably venous valves and the like. A stented valve has a support frame or stent that provides primary structural support in its expanded state. Such support frames are typically tubular when expanded, and may be expanded using a balloon or due to their own inherent elasticity (i.e., self-expanding) or by mechanical means. An exemplary stented valve is illustrated with respect to FIGS. 1A and 1B, although the present invention may be useful for crimping other such prosthetic valves.

Figure 1A:
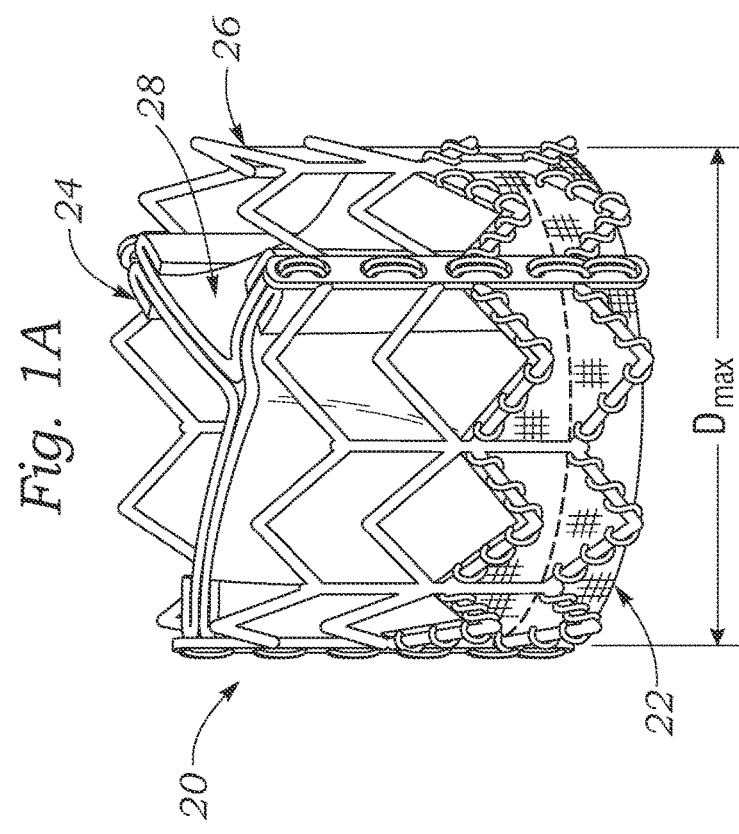
FIG. 1A is a perspective view of an exemplary prosthetic heart valve having an expandable support frame and a plurality of flexible leaflets therewithin.

FIG. 1A illustrates an exemplary balloon-expandable prosthetic heart valve 20 having an inflow end 22 and an outflow end 24. The valve includes an outer stent or support frame 26 supporting a plurality of flexible leaflets 28 within. FIG. 1A shows the valve 20 in its expanded or operational shape, wherein the support frame 26 generally defines a tube having a diameter $D_{max}$, and there are three leaflets 28 attached thereto extending into the cylindrical space defined within to coapt against one another. In the exemplary valve 20, three separate leaflets 28 are each secured to the support frame 26 and to the other two leaflets along their lines of juxtaposition, or commissures. Of course, a whole bioprosthetic valve such as a porcine valve could also be used. In this sense, "leaflets" means separate leaflets or the leaflets within a whole xenograft valve.

Figure 1B:
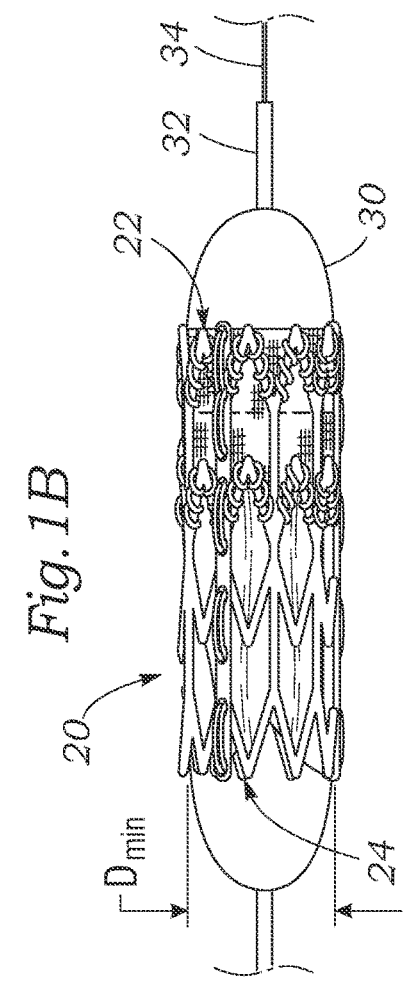
FIG. 1B is a side view of the prosthetic heart valve of FIG. 1A crimped to a reduced diameter around a balloon catheter.

FIG. 1B shows the valve 20 mounted on a balloon 30 prior to inflation. The crimped outer diameter of the valve 20 is indicated at $D_{min}$. The balloon 30 typically mounts on the end of a catheter 32 which is guided to the implant sites over a steerable wire 34.

Further details on the exemplary prosthetic heart valves of a similar type can be found in U.S. Pat. No. 6,730,118 and U.S. Patent Publication No. 2014/0343671, which are expressly incorporated by reference herein. In addition, the Sapien® line of heart valves available from Edwards Lifesciences of Irvine, Calif. are balloon-expandable prosthetic heart valves of a similar nature, whose construction is also expressly incorporated by reference herein.

U.S. Pat. No. 7,530,253 (expressly incorporated by reference herein) discloses a crimping mechanism for prosthetic heart valves which has the capacity to crimp a relatively large size valve down to a small delivery size. However, the mechanism in the '253 patent is relatively large due to the need to create high leverage forces to crimp the large diameter valves. In contrast, the crimper mechanisms disclosed herein create radial jaw motion using Cartesian movement guiding elements, close to the central aperture. Consequently, the size of the crimping jaws is reduced dramatically and the stiffness (or the ability to withstand higher crimping forces) of the jaws is increased.

The crimper mechanisms of the present application efficiently reduce the size of prosthetic valves from up to 30 mm ($D_{max}$) down to 6 mm ($D_{min}$). Prosthetic heart valve sizes are typically anywhere between 20 mm up to about 30 mm. The minimum reduction in size is thus around 14 mm and the maximum around 24 mm. In contrast, typical coronary stents have an expanded diameter of between about 3-6 mm and are crimped down to a minimum diameter of between about 1.5-2 mm, for a total maximum size reduction of around 4 mm. To distinguish conventional stent crimpers, the present invention provides a diameter reduction of at least 10 mm, and preferably at least 20 mm. Because diametrically opposed jaws act toward each other to reduce the size of the prosthetic valves, each crimp the valve half the distance of the entire reduction in diameter. This means each jaw moves radially inward at least 5 mm, and more preferably at least 10 mm.

Figure 2A:
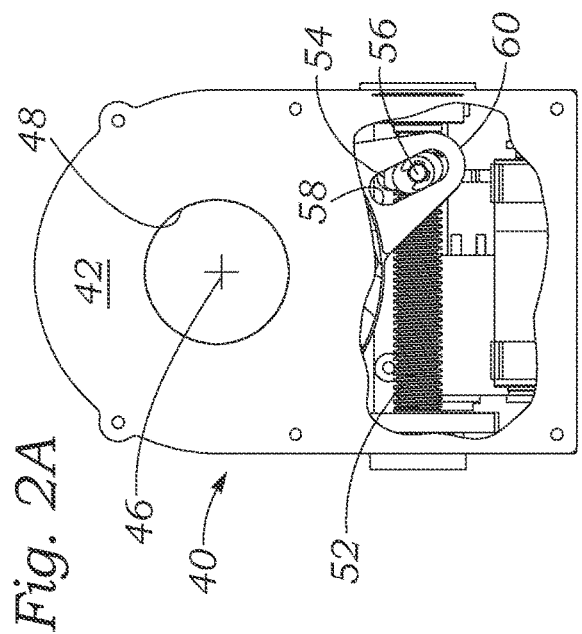
FIGS. 2A and 2B are partially cutaway views of a crimping mechanism of the present application in both open and closed crimping jaw positions.
Figure 2B:
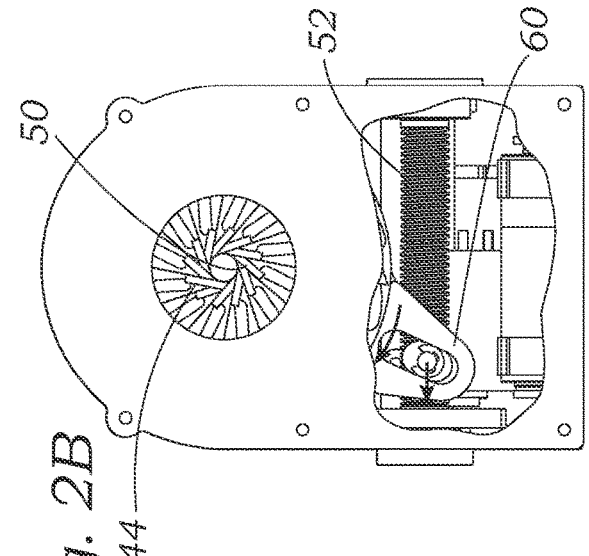

With reference now to FIGS. 2A and 2B, one preferred embodiment of an improved prosthetic heart valve crimping mechanism 40 is shown. The crimping mechanism 40 includes an outer housing 42 enclosing a plurality of crimping jaws 44 arranged about a central crimping axis 46. As will be described, there are preferably 12 crimping jaws 44, although other numbers of jaws are possible. The jaws 44 are initially shown retracted outward in FIG. 2A so as not to be visible within a receiving orifice 48 sized large enough to receive an expanded heart valve 20 such as shown in FIG. 1B. FIG. 2B illustrates the crimping jaws 44 displaced radially inward in a coordinated manner to form a crimping iris 50 defined by the combined inner surfaces of the assembly of jaws. The crimping iris 50 has a minimum diameter small enough to completely crimp the heart valve 20 onto the balloon 30. Although not shown, the crimping operation involves placing the expanded heart valve 20 around the balloon 30 before inserting the assembly into the orifice 48 and actuating the crimping jaws 44.

A lower portion of the outer housing 42 is cut away in both FIGS. 2A and 2B to expose a portion of an actuating mechanism therein. In particular, a relatively large diameter horizontally oriented lead screw 52 is journaled for rotation on either side of the housing 42 and perpendicular to the crimping axis 46. Although not shown, a motor in the lower part of the housing 42 is desirably connected via a power transmission to drive the lead screw 52 and increase applied forces. Alternatively, one or both ends of the lead screw 52 projects outward from the housing 42 and terminates in a nut or other such keyed element. By inserting a crank or key into one of the ends of the lead screw 52, it may be manually rotated about its axis. An internally threaded carriage 54 travels back and forth along the lead screw 52 when it rotates. The carriage 54 features a shaft stub 56 projecting from one side that is retained within a large slot 58 formed in a lever arm 60 of a cam wheel 62 (see FIGS. 3A and 3B), thus preventing rotation of the carriage with the lead screw.

Further details of the interaction between the cam wheel 62 and crimping jaws 44 will be explained more fully below. However, as seen in FIGS. 2A and 2B, rotation of the lead screw 52 causes the carriage 54 to travel from right to left which in turn interacts with the lever arm slot 58 and rotates the cam wheel 62 clockwise (CW). Rotation of the cam wheel 62 in this manner causes the jaws 44 to be displaced from their radially outward to their radially inward positions, thus crimping the heart valve 20.

Figure 3A:
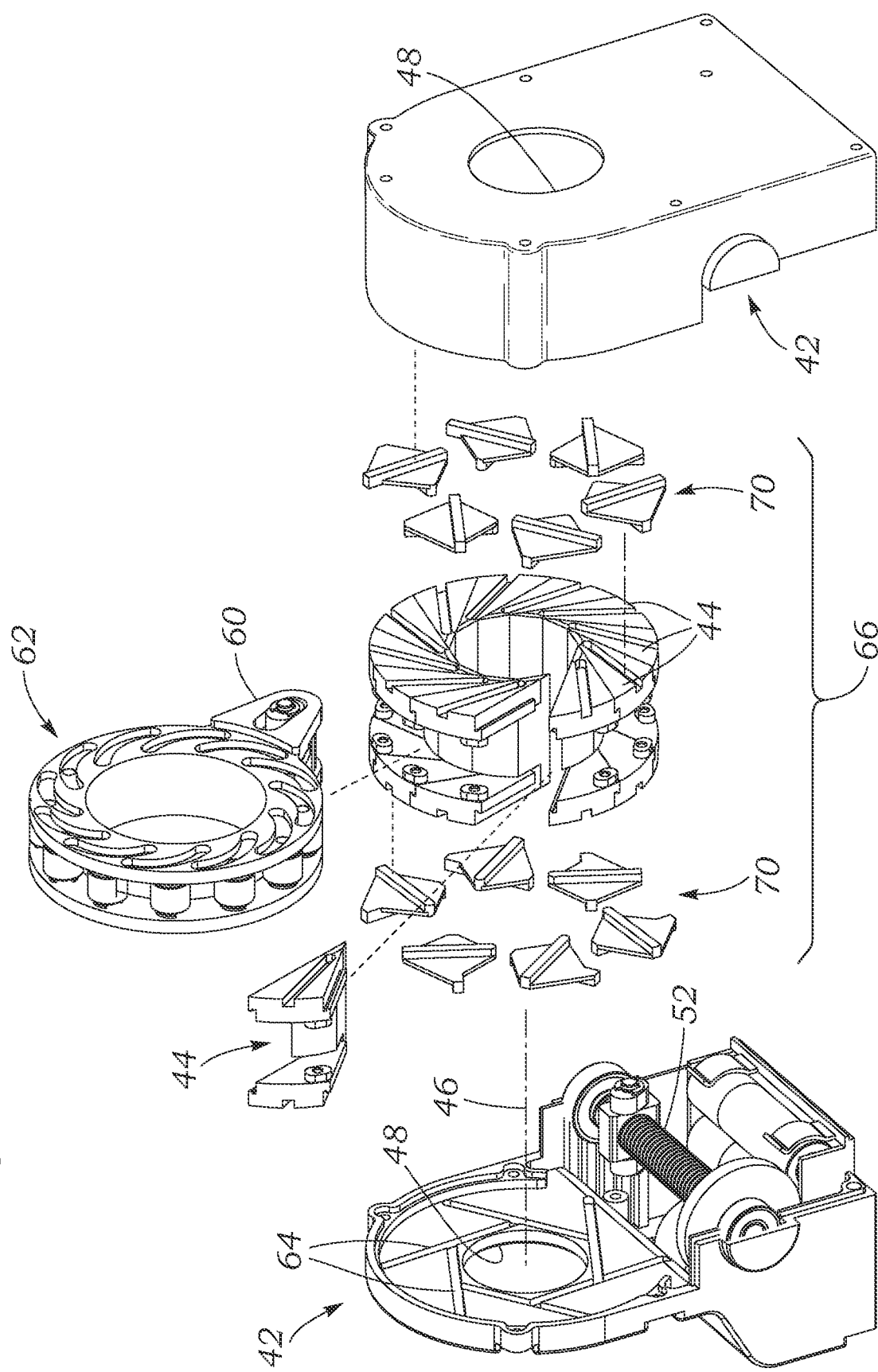
FIG. 3A is an exploded perspective view showing the components of the exemplary crimping mechanism.

FIG. 3A is an exploded perspective view showing the inner components of the exemplary crimping mechanism 40. The outer housing 42 includes two molded halves that together provide the bearing mounts for the lead screw 52. Although an inside face of only one of the housing halves is shown, both include a plurality of linear guide channels 64 molded into their inner faces and disposed in a spoke-like manner tangentially around the receiving orifices 48. The outer housing 42 halves sandwich therebetween a crimping jaw assembly 66.

FIG. 3B is a partially exploded perspective view of the crimping mechanism 20 showing the crimping jaw assembly 66 and one of the halves of the outer housing 42 with its guide channels 64. The crimping jaw assembly 66 has a generally cylindrical profile that fits closely within a similarly-shaped upper portion of the outer housing 42, and is centered along the crimping axis 46. The crimping jaw assembly 66 is made up of the moving parts within the crimping mechanism 40, aside from the lead screw 52 and carriage 54. With reference also to FIG. 3A, the crimping jaw assembly 66 comprises an axial sandwich of elements in the middle of which is the cam wheel 62. The crimping jaws 44 flank the cam wheel 62, and a number of Cartesian guide elements 70 are arranged on the outside of the crimping jaws 44. In turn, the crimping jaw assembly 66 is firmly located within the two halves of the housing 42, but may rotate therein.

To understand the interaction between the moving parts of the crimping jaw assembly 66, it is necessary to start from the cam wheel 62 and move axially outward. The cam wheel 62 is rotated by the lead screw 52 and carriage 54, and thus forms the prime mover of the crimping jaw assembly 66. In general, rotation of the cam wheel 62 initiates movement of all the other pieces, although as will be described below physical interaction and guiding contact between the pieces creates additional reaction forces that distribute the forces from the cam wheel.

FIG. 3C is a perspective view of the exemplary cam wheel 62, which includes a pair of parallel annular discs 72 joined on their inner circular edges by an annular hub 74. A plurality of axially-oriented rollers 76 are journaled for rotation between the two discs 72 and circumferentially distributed in an annular space 78 defined radially outside of the hub 74. Each of the roller 76 projects slightly outward from the outer edges of the discs 72 so as to contact the outer housing 42 to facilitate rotation therein and provide stability to the crimping operation. As also seen in FIG. 4, each of the annular discs 72 includes a series of arcuate cam slots 80 formed therein which curve generally from their radially inner to their radially outer edges. Each of the cam slots 80 is curved so as to be radially outwardly convex. The arcuate cam slots 80 on the two discs 72 are aligned and have the same shape such that looking at the outer face of one disc the cam slots 80 extend radially outward in a clockwise (CW) direction (i.e., FIG. 4), while looking at the outer face of the other disc the slots extend radially outward in a counter-clockwise (CCW) direction.

In the illustrated embodiment, there are twelve cam slots 80 nested relatively closely to each other around each disc 72. Each two aligned slots 80 in the two discs 72 act on one of the jaws 44, and therefore in the preferred embodiment there are twelve jaws 44. It should be understood that the number of crimping jaws 44, and thus the number of cam slots 80, may be modified but is preferably between 8-16.

As seen in FIGS. 5A-5C, each of the crimping jaws 44 includes a radially inner crimping wedge 82 connecting a pair of axially spaced apart, generally triangular outer traveler blocks 84. The elevational view of FIG. 5C shows that the traveler blocks 84 each span an included angle θ which varies depending on how many jaws 44 are utilized, and is preferably 30° with twelve jaws. When the jaws 44 are assembled along with the cam wheel 62, as seen in FIG. 6 with the jaws 44 in their radially outward positions, the crimping wedges 82 are positioned within a central aperture defined inside the annular hub 74 of the cam wheel 62. The inner surfaces of the crimping wedges 82 define the aforementioned iris 50 of the crimping mechanism 40. The traveler blocks 84 of each of the jaws 44 closely flank the annular discs 72 of the cam wheel 62, and small cam followers 86 extending axially inward from each of the blocks insert into the arcuate cam slots 80. Each of the cam followers 86 has a generally rounded configuration and is angled in a manner that aligns with a tangent to the curve of the arcuate cam slots 80. The cam followers 86 are sized so as to be slightly smaller than the width of the cam slots 80, and may be made of a lubricious material such as Nylon or Teflon to facilitate sliding therein. The cam followers 86 are located at a radially outer extent of each of the traveler blocks 84.

At this stage, a further word about materials is relevant. Many of the components are molded of a suitable polymer, such as the outer housing 42 and cam wheel 62. The lead screw 52, carriage 54 and of course motor parts will preferably be metallic, though some may also be polymer. The crimping jaws 44 may be a molded polymer, though the inner crimping wedge 82 which contacts the article being crimped is desirably a material with high strength & stiffness along with low friction, such as reinforced Nylon. In this respect, the inner crimping wedges 82 may be inserts to the larger jaws 44. Likewise, as mentioned, the cam followers 86 are preferably stiff and low friction, such as Nylon. Of course, alternatives exist and these are just exemplary materials.

It will thus be clear that rotation of the cam wheel 62 causes a radially inward motion of the crimping jaws 74 due to the interaction between the arcuate cam slots 80 and the cam followers 86. FIGS. 7A and 7B are elevational views of the inner crimping mechanism 40 showing the central cam wheel 62 and crimping jaws 44 assembled thereon in both open and closed crimping jaw positions. Only one of the arcuate cam slots 80 as well as the cooperative cam follower 86 on one of the jaws 44 is shown in phantom. It should be understood that although only one each is shown, there are two cam slots 80 and two cam followers 86 associated with each jaw 44. The jaw 44 on which the cam follower 86 is shown is highlighted by extending dashed lines along respective angled edges to form angles $\alpha$ and $\beta$ with the horizontal.

FIGS. 7A and 7B show the lever arm 60 of the cam wheel 62 rotating in a clockwise (CW) direction such that the cam followers 86 on each jaw 44 are acted on by the arcuate cam slots 80. Because the cam slots 80 curve radially inward as the wheel 62 rotates clockwise, a radially inward camming force is transmitted to the cam followers 86. Because of the sliding interactions between the jaws 44, inward movement of all of the jaws 44 from their rigid connection to their respective cam followers 86 is the same. It should be noted that the highlighted crimping jaw 44 remains in the same rotational orientation while it translates radially inward and downward. That is, the angles $\alpha$ and $\beta$ that describe the orientation of the jaw 44 relative to horizontal remain the same. The same is true for all of the jaws 44. As a result of this movement, the inner surfaces of the crimping wedges 82 define a radially constricting iris 50. Additionally, although the absolute angle of a tangent line drawn with respect to the curvature of the arcuate slot 80 varies from one end of the slot to the other, the orientation of the cam follower 86 remains parallel to these tangent lines because of the movement of the respective jaw 44. This facilitates sliding movement of the cam followers 86 within the slots 80.

The crimping jaws 44 have cooperating sliding surfaces such that they all moved together with the same degree of translation as one another, albeit along different angles. In particular, each of the angular edges of the traveler blocks 84 cooperates with the adjacent traveler block edges in a tongue and groove fashion. With reference back to FIGS. 5A and 5B, each of the traveler blocks 84 has a sliding rail 88 thereon that mates with an oppositely-oriented sliding rail on the traveler block 84 on the adjacent jaw 44. This interaction can be seen in the perspective view of FIG. 6. The sliding engagement of the rails 88 helps prevent binding between the jaws 44 as they move inward together.

Furthermore, the starting positions of the crimping jaws 44 and the angles of the edges of the traveler blocks 84 causes the assembly of jaws to rotate when they are cammed inward. In essence, each of the crimping jaws slides inward relative to one of its adjacent crimping jaws, and the resulting displaced shape seen in FIG. 7B somewhat resembles a pinwheel. The reader will also see from comparison of FIGS. 7A and 7B where the highlighted crimping jaw 44 translates radially inward and downward, amounting to a clockwise rotation thereof.

As seen in FIGS. 5A-5C, the crimping jaws 44 also have linear guide slots 90 on the outer faces of both of the traveler blocks 84. These guide slots 90 interact with the aforementioned Cartesian guide elements 70, as will be explained below. With specific reference to FIG. 5C, the guide slot 90 of each jaw 44 bisects included jaw angle $\theta$.

Figure 8:
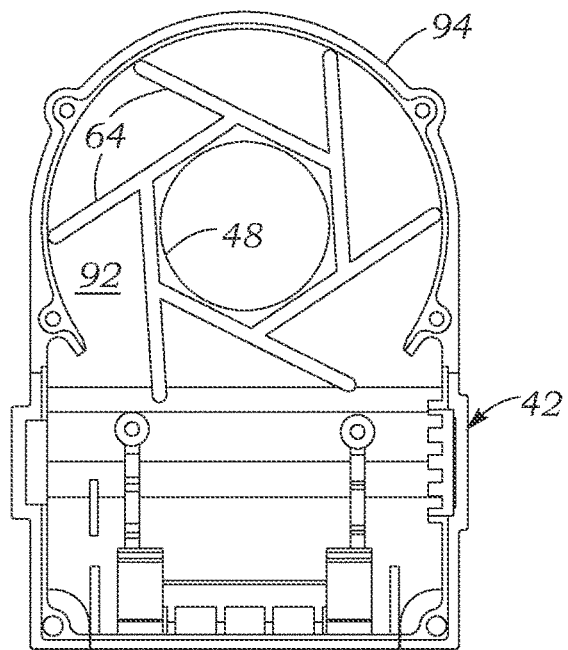
FIG. 8 is an elevational view of an inner face of one half of the outer housing of the exemplary crimping mechanism showing fixed guide channels thereon.

FIG. 8 is an elevational view of an inner face of one half of the outer housing 42 showing the fixed guide channels 64. As mentioned above, the guide channels 64 lie tangent to the central orifice 48 in the housing 42. The guide channels 64 preferably comprise axial depressions in an outer plate 92 of the housing 42, with the housing halves including the guide channels desirably being injection molded. Radially inner ends of each guide channel 64 merge with an adjacent guide channel at about a mid-point thereof. Because there are six guide channels 64 spaced equidistantly and oriented evenly around the orifice 48, the inner portions of the guide channels define vertices of a hexagon closely surrounding the orifice. Each guide channel 64 extends from a vertex of the hexagon past its point of tangency with the orifice 48 and outward to an outer rim 94 of the housing 48. The guide channels 64 interact with the Cartesian guide elements 70, as will be explained below. The number of guide channels depends on the number of jaws; namely, half the of number of jaws.

Figure 9A:
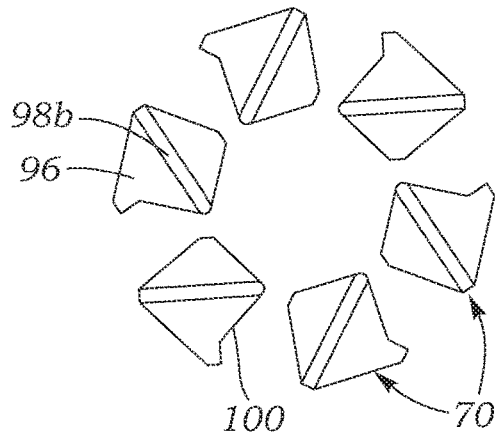
Figure 9B:
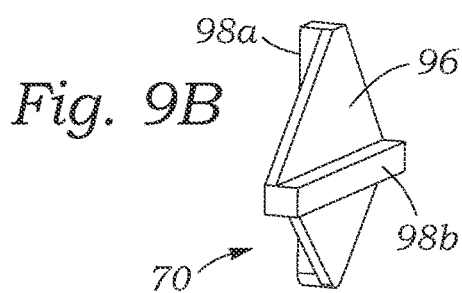
FIG. 9B is a perspective view of a single Cartesian guide element.
Figure 10A:
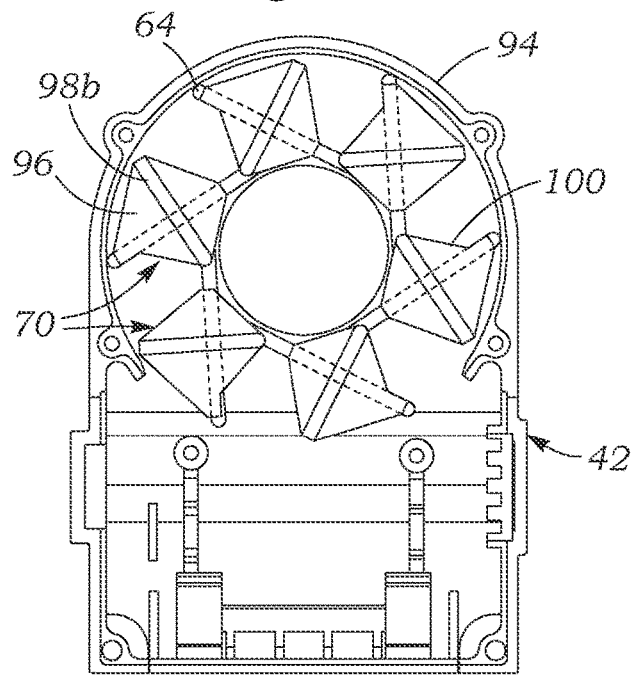
FIG. 10A is an elevational view of the inner face of the outer housing of the crimping mechanism showing the locations of the guide elements thereon when in radially outward positions.
Figure 10B:
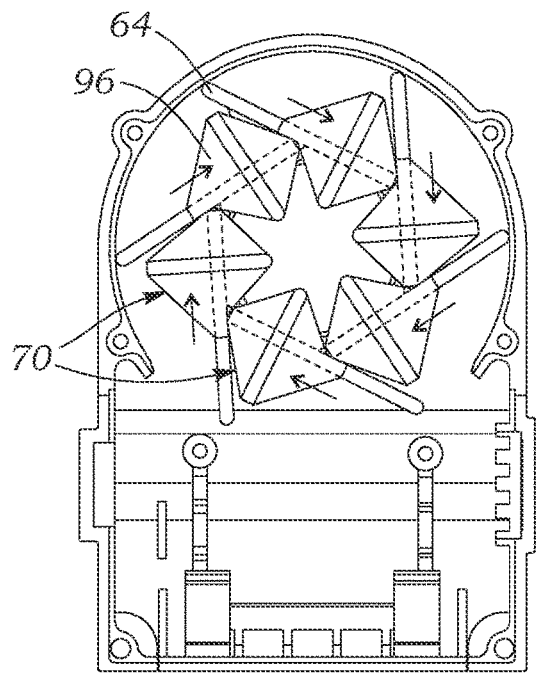
FIG. 10B is a similar view showing the guide elements in radially inward positions.
Figure 13C:
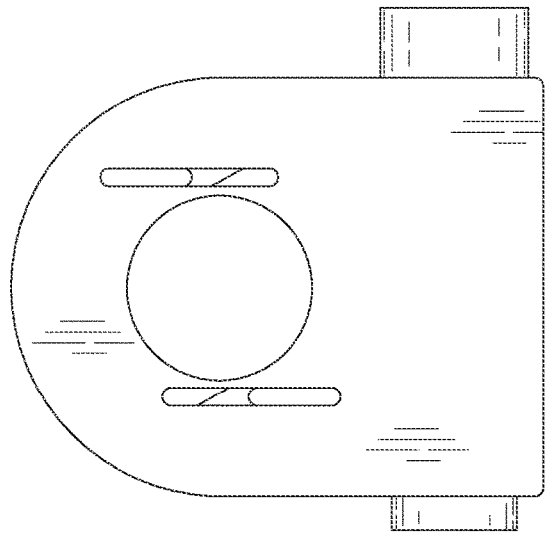
FIGS. 13A-13C are several views of a further embodiment of a crimping mechanism of the present application similar to that shown in FIGS. 1A-12B but with fewer guide elements.
Figure 13B:
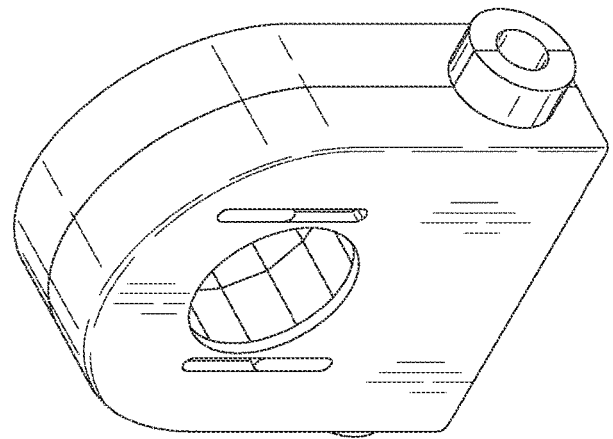
Figure 13A:
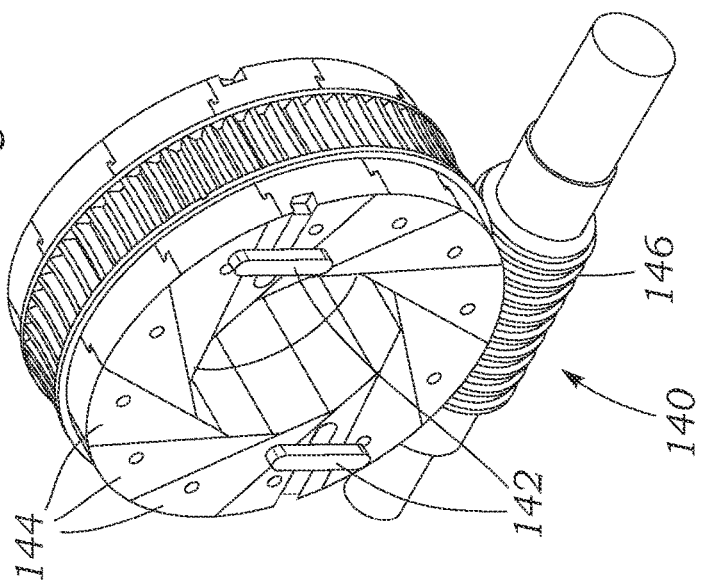

FIG. 9A shows a plurality of the Cartesian guide elements 70 arranged in space in the same manner as they would be when interacting with the outer housing 42, FIG. 9B shows an individual Cartesian guide element 70 in isolation, while FIGS. 10A and 10B superimpose the guide elements onto the outer housing and channels 64. Each of the guide elements 70 comprises an angular generally flat rectilinear plate 96 having a pair of raised linear bars 98a, 98b projecting from opposite inner and outer faces. The opposed linear bars 98a, 98b are oriented perpendicular to each other, and thus together define a right-angle cross, albeit on opposite faces of the guide elements 70. Outer faces of the guide elements 70 abut the outer plate of the housing 42 such that the outer linear bars 98a on that side fit closely within the fixed guide channels 64. On the inner face, the guide elements 70 contact the assembly of the crimping jaws 44, and the inner linear bars 98b fit closely within the guide slots 90 on six of the guide elements. Because the outer linear bars 98a are constrained within the guide channel 64, the guide elements 70 are also constrained to move linearly between first and second positions parallel to the guide channels.

FIG. 10A shows the locations of the guide elements 70 superimposed on the outer housing 42 when in radially outward positions (as also in FIG. 9A). As mentioned, the outer linear bars 98a extend within and are guided by the guide channels 64. In this starting position, radially outer edges of the rectilinear plates 96 are close to the outer rim 94 of the housing 42, and their radially inner edges are positioned just outside of the central orifice 48. FIG. 10B is a similar view showing the guide elements 70 in radially inward positions. The outer linear bars 98a slide inward along the guide channels 64, and the rectilinear plates 96 fit closely together. The rectilinear plates 96 define an irregular diamond shape with generally four vertices at the outer extents of the crossed linear bars 98a, 98b. Straight sides extend between the vertices, and there is an indentation 100 on one side adjacent one of the vertices. When the guide elements 70 are in their radially inner positions, one of the vertices of each fits closely within this indentation 100 on the next, and the nested contact between all of the guide elements 70 in this manner provides a positive stop on further inward movement of the crimping mechanism 40.

FIGS. 11A and 11B are elevational views similar to FIGS. 7A and 7B with the crimping jaw assembly 66 in place but also showing the Cartesian guide members 70 interacting with the crimping jaws 44. The guide members 70 are termed "Cartesian" because of the opposite crossed linear bars 98a, 98b on each. That is, as described above, the guide member 70 are constrained to move linearly along the guide channels 64 in the outer housing 42. At the same time, interaction between the inner linear bars 98b on each member 70 and the guide slots 90 on every other crimping jaw 44 constrains those jaws to move in the direction of the associated guide member 70.

Prior to discussion of this coordinated movement, it should be noted that there are only six guide members 70, while there are twelve crimping jaws 44. Therefore, as seen in FIG. 11A, each of the guide members 70 interacts with every other crimping jaw 44. The six crimping jaws 44a that interact with the guide members 70 can be termed guided jaws, while the six crimping jaws 44b that do not interact with the guide members are termed follower jaws. However, it is important to remember that each of the crimping jaws 44 has cam followers 86 thereon, and thus each of the crimping jaws is driven directly by the cam wheel 62.

With reference again to FIGS. 11A and 11C, Cartesian axes 102, 104 are superimposed over one combination of guide member 70 and its guided jaw 44a. A first axis 102 extends along the outer linear bar 98a on the guide member 70. The reader will understand that the outer linear bar 98a interacts with the guide channels 64 on the half of the outer housing which is not shown. Therefore, the guide member 70 is constrained for linear movement along the first axis 102. A second axis 104 extends along the inner linear bar 98b on the guide member 70, which corresponds to the guide slot 90 on the guided jaw 44a. The second axis 104 translates with the guide member 70, always remaining perpendicular to the first axis 102. Both the guided jaw 44a and the guide member 70 move together. This arrangement reduces frictional losses and allows an option to combine the guided jaws 44 and the guide elements 70.

Now with respect to FIGS. 11B and 11D, the cam wheel 62 has rotated clockwise causing sliding movement of all of the crimping jaws 44. As the guided jaw 44a begins to move inward, it is constrained to move along the first axis 102 with the corresponding guide member 70. Likewise, all of the six guided jaws 44 are constrained to move with their corresponding guide members 70. As each guided jaw 44a starts to move inward it slides relative to one of the two adjacent follower jaws 44b. Of course, each follower jaw 44b is acted on by two adjacent guided jaws 44a. Because of the angled sides of the adjacent jaws 44, as explained above with respect to FIGS. 7A and 7B, the assembly of jaws begins to rotate clockwise. The circumferential component of movement of each of the guided jaws 44 transfers forces via the guide slots 90 to the inner linear bars 98b on the guide members 70. This starts the guide members 70 translating along the first axis 102.

It should be mentioned that the provision of two sets of force actuators (disks 72, traveler blocks 84, and guide members 70) results in a symmetric, balanced system and the stresses are reduced. Of course, a single disk 72 and associated crimping elements is possible, but would require a more robust structural design.

As the guide members 70 and the guided jaws 44a translate along the first axes 102, they continue to move inward relative to the outer housing 42. Of course, although they are not directly in contact with the guide member 70, the follower jaws 44b move in a like manner because they are also acted on by the cam wheel 62, and from the symmetry and mating edge contact between the jaws. FIG. 11E isolates a central one of the guided crimping jaws 44a from FIGS. 11C and 11D and shows the jaw with its absolute movement 106 along the first axis 102. Continued rotation of the cam wheel 62 eventually moves the crimping jaws 44 into the positions shown in FIGS. 7B and 11B. It is also worth noting that the tip of the crimping wedge 82 on each jaw translates radially inward along a radial line 110 through the central crimping axis 46 (see FIG. 11A). That is, the composite movement 106 is parallel to the radial line 110 through the crimper axis 46. This ensures even crimping of the stent or valve.

The relative movements of the cooperating elements in the crimping mechanism 40 will occur regardless if there is an object being crimped or not. However, when an object such as the expanded heart valve 20 of FIG. 1A is being crimped, it applies substantial resistance to the crimping mechanism 40. More specifically, the hoop strength of the expanded heart valve 20 provides a radially outward reaction force 108 directly to the crimping wedges 82 of the jaws 44, as indicated in FIG. 11E.

Without the guide members 70, the mechanism is not balanced and the reaction force 108 will tend to rotate the jaws 44. Further, without the guide members 70 this reaction force would be translated through the crimping jaws 44 to the cam followers 86, and thus to the arcuate cam slots 80 of the cam wheel 62. Although the cam slots 80 are relatively robust, the cam followers 86 are not only susceptible to deformation from stress, but also binding. However, because of the contact between the guide members 70, crimping jaws 44 and fixed outer housing 42, the reaction forces from the crimping process are transferred and distributed such that the stress on the cam followers 86 is reduced. In particular, the Cartesian guide members 70 absorb a considerable amount of the stress and provide an effective companion for the crimping jaws 44. With respect to FIG. 11E, the radially outward reaction force 108 from the crimping process translates into a torque on the crimping jaw 44a. This torque is resisted primarily by the rigid constraint imposed on the guide member 70 by the outer housing guide channels 64 to move along the first axis 102. To be more explicit, the clockwise torque on the guided jaw 44a would be translated directly to the corresponding guide member 70 because of the interaction between the guide slot 90 and the inner linear bar 98b, and the rotational torque within be resisted by the guide member 70 because it is fixed rotationally with respect to the outer housing 42.

One benefit over previous crimpers is in the smaller mechanism size (~½ the size of current crimpers) and in the ability to operate under high crimping forces (small and stiff crimping jaws). The jaws 44 are displaced essentially radially using the Cartesian guiding element 70 positioned close to the central orifice 46. This guided concept enables dramatic reduction of the size of the crimping jaws 44 and the stiffness (or the ability to withstand higher crimping forces) of the jaws is increased. The radial alignment mechanism provided by the guiding elements 70 is based on steep angular movement translated to radial forces imposed close to the central crimping axis. The guiding elements 70 translate the angular movement from the cam wheel 62 to a radial force, by essentially separating it into a Cartesian movement. In this movement, the jaws 44 are moving radially similarly to the previous crimpers, and the guiding elements 70 move with them, in the tangential housing channels 64.

In a preferred embodiment, the width of the crimping mechanism 40, or approximately the diameter of the cam wheel 62, is about 80 mm. A total height of the crimping mechanism 40, such as shown in FIG. 2A which includes the cam wheel 62 above the lead screw 52 and associated actuators, is about 115 mm. Of course, those exemplary sizes are for a mechanism capable of crimping a balloon-expandable prosthetic heart valve 20 such as shown in FIG. 1A down to a delivery size shown in FIG. 1B. The mechanism must be robust enough to crimp a stainless steel support frame of the heart valve 20 from, for example, 30 mm ($D_{max}$) down to 6 mm ($D_{min}$). Less stiff frames or less of a size reduction may enable the crimper to be even further reduced in size and, conversely, a larger size reduction may require a larger crimper.

FIGS. 12A and 12B are schematic perspective views of an alternative embodiment of a crimping mechanism 120 in both open and closed positions of crimping jaws 122, respectively. The entire crimping mechanism 120 is not shown, but will be similar to that shown in FIGS. 1-11. The main difference in the crimping mechanism 120 is a modification to the guide members 124. That is, rather than having a diamond-shape plate with opposing crossed linear bars, as before, the guide members 124 are simply perpendicular bars attached together. The inner bars will extend within guide slots 126 in the crimping jaws 122, while the outer bars will slide within fixed guide channels in an outer housing (not shown). In all other respects, the crimping mechanism 120 works the same as was described above.

Figure 14B:
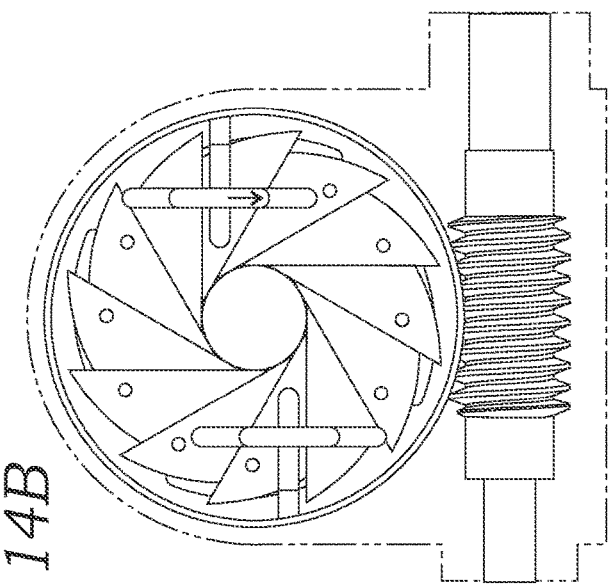
FIGS. 14A-14C are partial elevational views of the crimping mechanism of FIGS. 13A-13C in both open and closed crimping jaw positions.
Figure 14C:
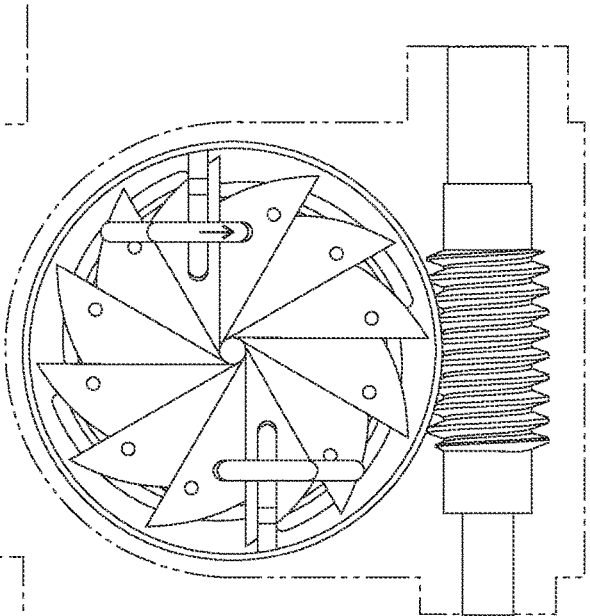
Figure 14A:
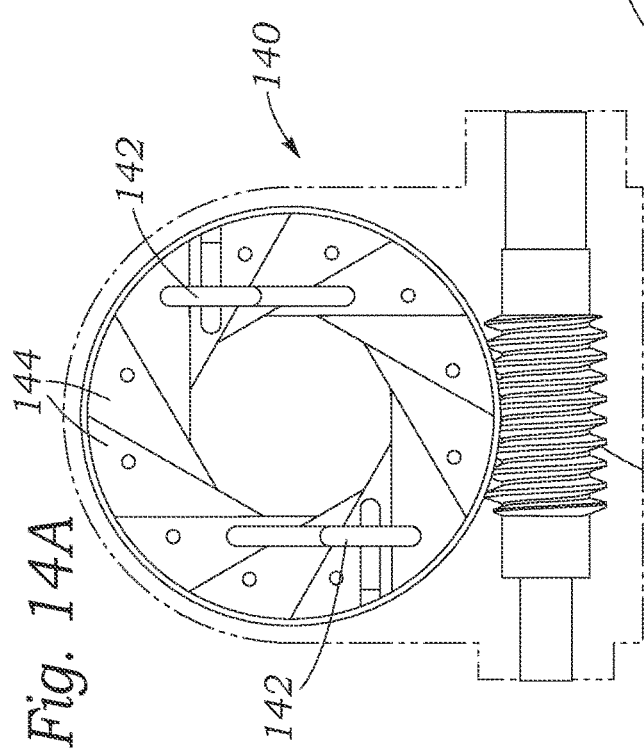

FIGS. 13A-13C and 14A-14C illustrate a further crimping mechanism 140 similar to that shown in FIGS. 1A-12B but with fewer guide elements 142. The guide elements 142 are simple crossed linear bars, as described above with respect to FIGS. 12A and 12B. Further, there are still twelve crimping jaws 144. In contrast to the earlier embodiments, however, there are only two guide elements 142. Operation of the crimping mechanism 140 as seen in FIGS. 14A-14C is similar to that described above, where a lead screw 146 turns a cam wheel (not shown) which initiates the inward movement of the crimping jaws 144. Because the crimping jaws 144 are all linked in a tongue and groove fashion as was described above, they would move in sync in and out even without guide elements 142. The guide elements 142 only mesh with two of the crimping jaws 144, but still provide a reduction in stress and distributed application of force. Two guide elements 142 is considered a minimum, and three, four, or six are contemplated for a twelve jaw mechanism. A practical maximum number of guide elements 142 is six in the illustrated embodiments, or half the number of jaws. This is so that the guide elements 142 do not interfere with each other as they slide back and forth.

Figure 15A:
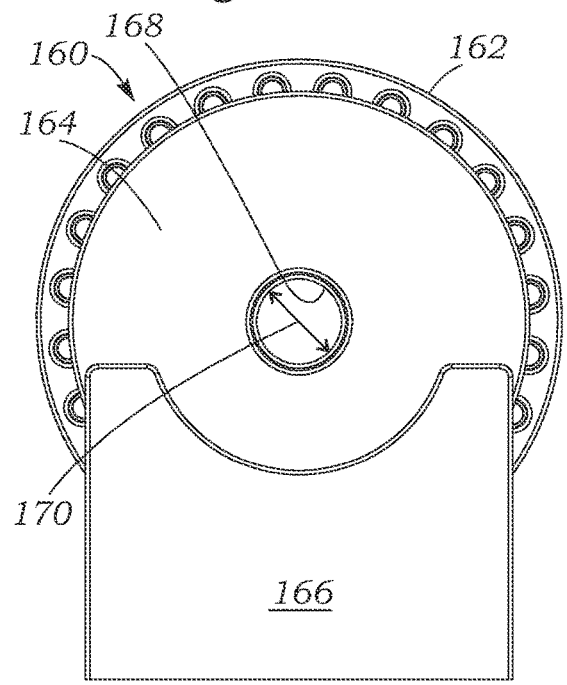
FIGS. 15A-15B are elevational views of a still further crimping mechanism of the present application that utilizes a compressible sleeve, shown in both open and crimped states.
Figure 15B:
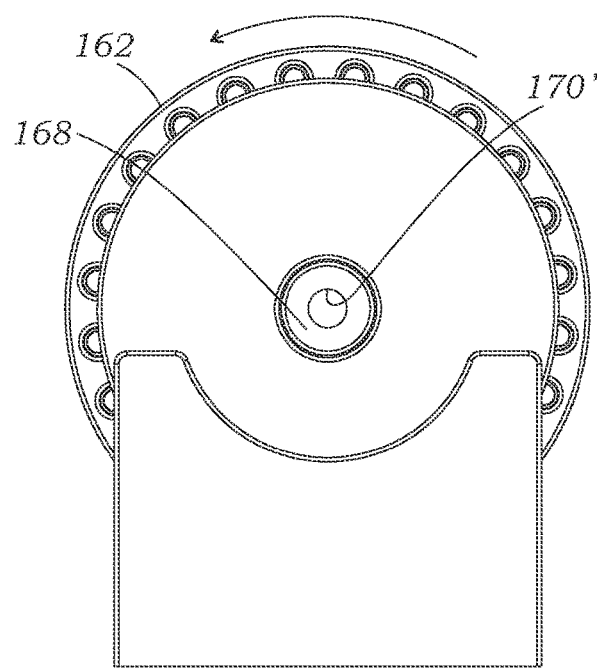
Figure 16A:
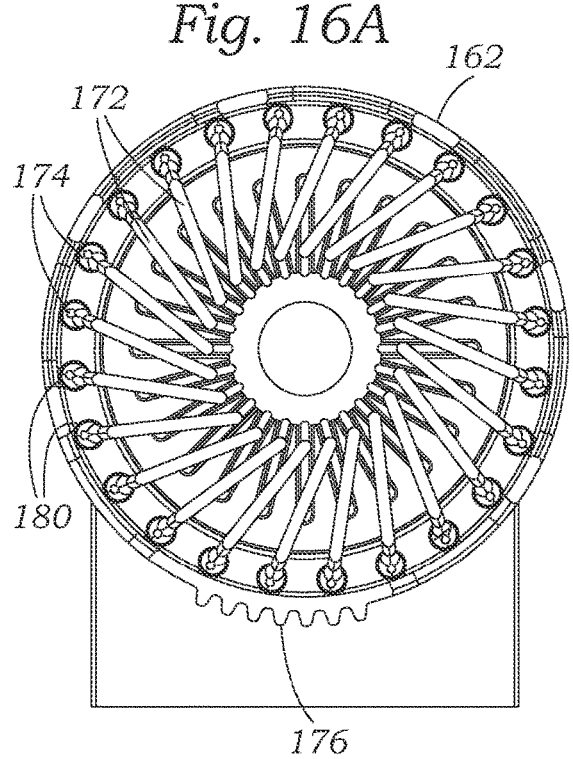
FIGS. 16A-16B are elevational views of the crimping mechanism with a compressible sleeve with a front cover removed to show internal components in the positions of FIGS. 15A and 15B, respectively.
Figure 16B:
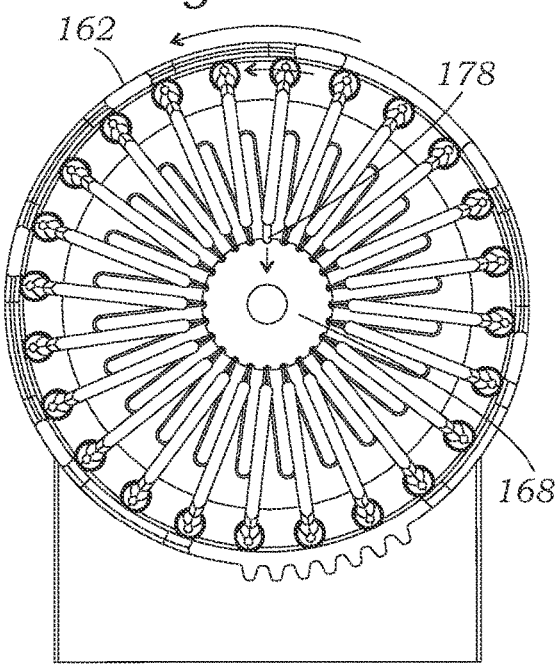

FIGS. 15A-15B schematically depict a still further crimping mechanism 160 of the present application that utilizes a compressible sleeve, such as a soft elastomer, rather than a plurality of separate jaws. FIGS. 16A-16B are elevational views of the crimping mechanism 160 with a front cover removed to show internal components in the positions of FIGS. 15A and 15B, respectively. The crimping mechanism 160 features a cam wheel 162 that rotates within a pair of end plates 164 (only one shown). The end plates 164 are fixed over a housing 166 within which is located an actuation mechanism, much like the lead screw assembly described above.

A compressible sleeve 168 is held rotationally still between the end plates 164 and comprises an annular elastomeric sleeve with outer axial grooves. An inner lumen or orifice 170 defined by the sleeve 168 constricts upon rotation of the cam wheel 162 to a smaller size orifice 170', as seen in FIGS. 15B and 16B.

With reference to FIGS. 16A-16B, as well as to FIGS. 17-19B, a plurality of linkage plates 172 are arranged for coordinated movement within the cam wheel 162. More particularly, outer ends 174 of the plates 172 are journaled for rotation in corresponding bores 180 around the outer perimeter of the cam wheel 162. The cam wheel 162 may have a short segment of gear teeth 176 on its lower edge which can be engaged by a moving rack, lead screw or other such gearing within the housing 166.

FIG. 17 shows the crimping mechanism 160 exploded. An array 182 of the linkage plates 172 and cooperating compression plates 178 (see FIGS. 19A-19B) includes at least 12, and preferably at least 24 of the linked plates. The array 182 is arranged within the cam wheel 162 which includes two series of the perimeter bores 180 within which two outer ends 174 of each linkage plate 172 are journaled for rotation. In this way, the symmetry reduces any possible misalignment forces during crimping of the prosthetic heart valve. Each end plate 164 has a central aperture for passage of the prosthetic heart valve into the middle of the crimping mechanism 160, as well as an array of radial slots 186 which will be described below.

Figure 19A:
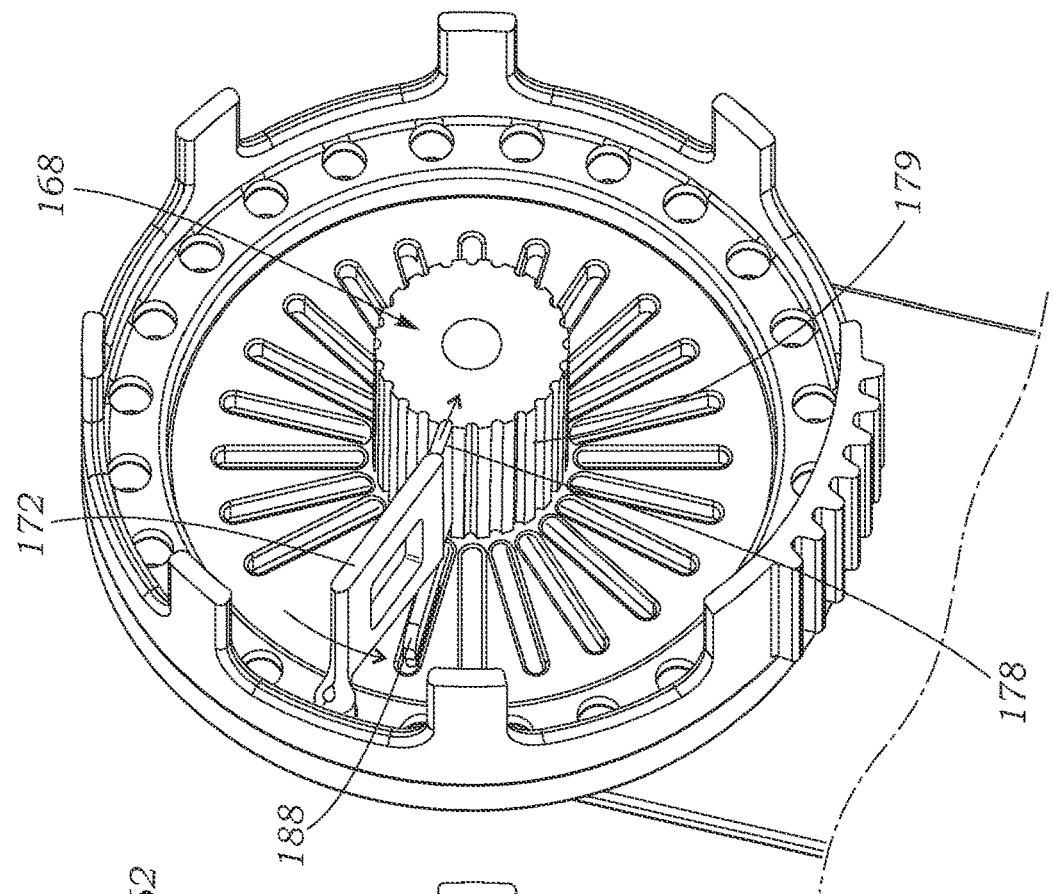
FIGS. 19A-19B are cutaway perspective views of the crimping mechanism with a compressible jaw showing the movement of one compression assembly.
Figure 19B:
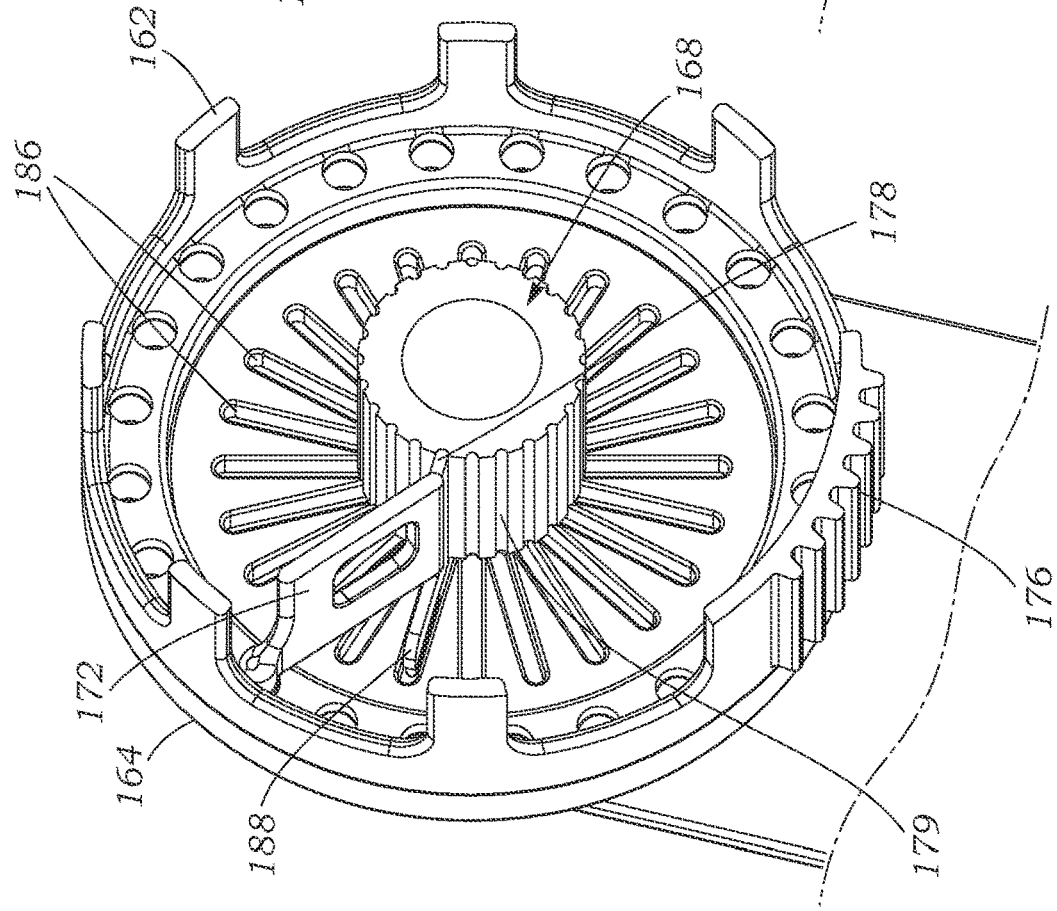

As seen best in the cutaway views of FIGS. 19A-19B, each linkage plate 172 is hinged on an inner end to a compression plate 178. The inner end of each compression plate 178 engages one of the axially-oriented grooves 179 around the outside of the compressible sleeve 168. The compression plate 178 is formed with two outer rails 188 that slide within the radial slots 186 formed in the end plates 164. Rotation of the cam wheel 162 displaces the outer ends 174 of the linkage plates 172 such that they transition from the angled orientation shown in FIG. 16A to the radial orientation of FIG. 16B. Because the inner ends of the linkage plates 172 are hinged to the compression plates 178, the compression plates 178 are forced radially inward. Engagement between the outer rails 188 and the slots 186 constrains the compression plates 178 for radial movement. The linked plates 172, 178 surrounding the sleeve 168 thus push inward on the grooves 179 and compress the sleeve radially to reduce the central orifice diameter.

Although the crimping mechanism 160 represents an elegant solution, with a single crimping "jaw" reducing the number of moving parts and associated friction, there are limitations on the magnitude of crimping, and a series of similar crimpers may be required to reduce the size of the article in stages. Of course, if only a small amount of crimping is necessary, one crimping mechanism will be suitable.

FIGS. 20A-20C are perspective and cutaway views of a multi-stage crimper 200 with an outer housing 202 enclosing a series of progressively sized crimping mechanisms 204a, 204b, 204c each with a compressible "jaw." A crimping orifice 206a, 206b, 206c for the three crimping mechanisms gradually reduces the size of a prosthetic device such as the prosthetic heart valve described above. FIG. 20B shows a front cover of the housing 202 removed to illustrate one rotating cam wheel 210 on the smallest crimping mechanism 204a. A lower segment of gear teeth 212 on the cam wheel 210 may be acted on by a linearly displaced rack 214 to rotate the cam wheel. Although not shown, the larger crimping mechanisms may also have similar cam wheels which are acted on simultaneously by the single rack 214. FIG. 20C shows a front portion of the cam wheel 210 removed to expose a plurality of linked plates 216, which may be the same as those described above with respect to FIGS. 15-19.

To crimp a prosthesis, it is first placed in the largest crimping mechanism 204c and the rack 214 displaced to reduce the size of the prosthesis a first amount. The rack 214 returns to its original position and the prosthesis is then transferred to the middle crimping mechanism 204b and its size is further reduced. Finally, the smallest crimping mechanism 204a reduces the size of the prosthesis to its final diameter. Although three crimping mechanisms are shown, a minimum of two stages and more than three may be used for sequentially crimping a prosthesis in this manner.

Figure 21A:
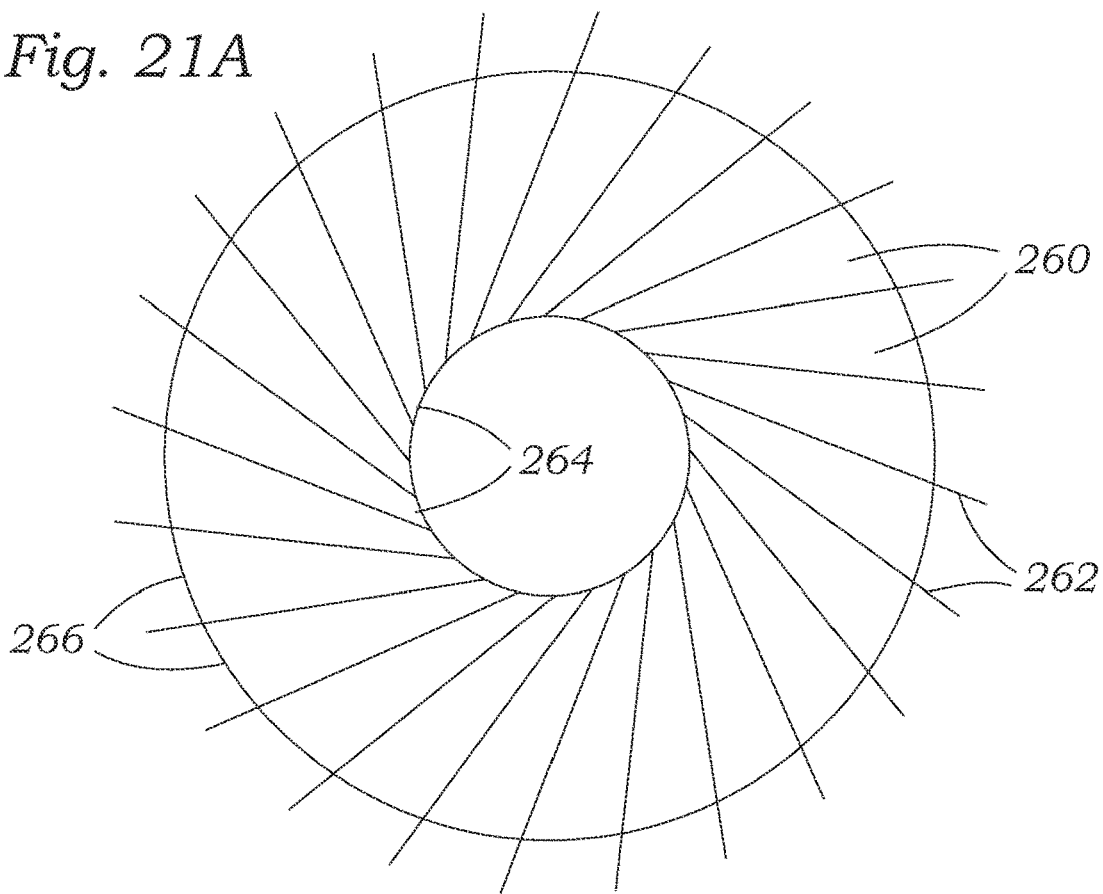
FIGS. 21A-21B are schematic elevational views of a still further crimping mechanism of the present application that utilizes compressible jaws.
Figure 21B:
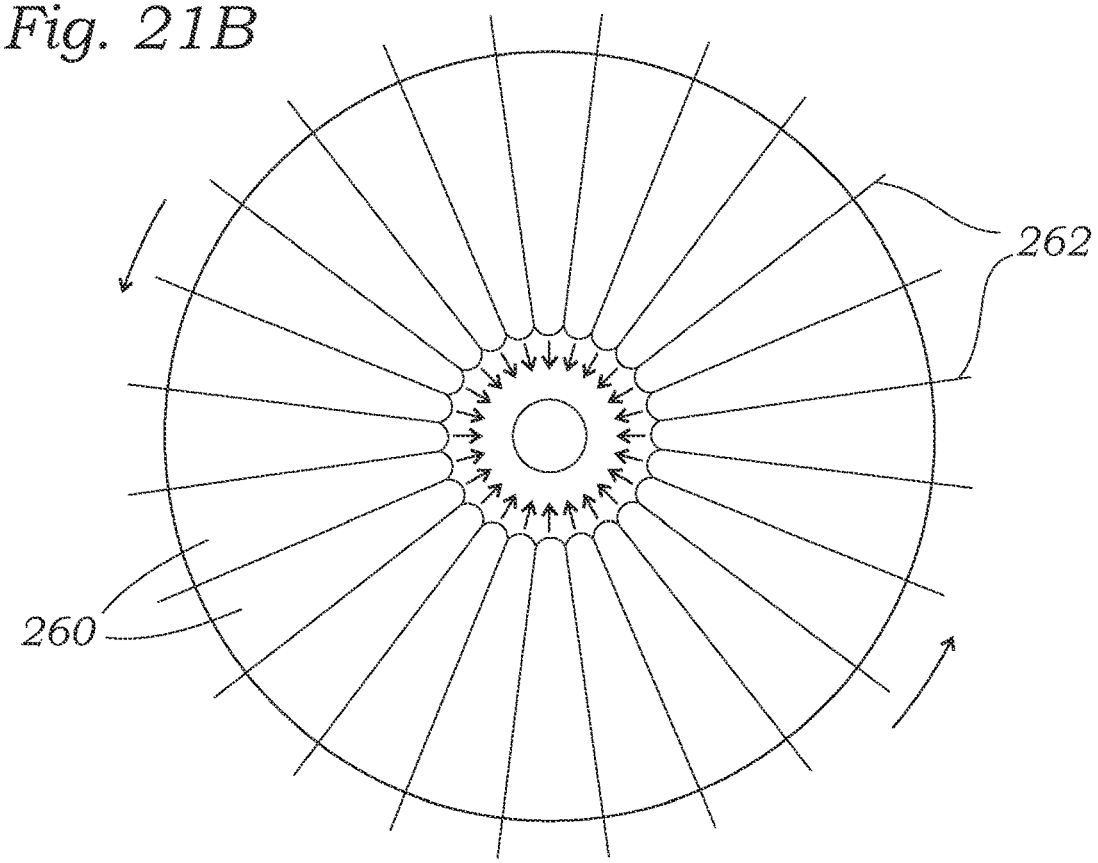

FIGS. 21A-21B schematically depict a still further crimping mechanism of the present application that utilizes compressible jaws 260, such as a soft elastomer. The jaws 260 are positioned between a series of spoke-like plates 262 which are initially angled from the radial so as to be nearly tangential to a circle defined by the inner faces 264 of each of the compressible jaws 260. Outer faces 266 of each of the jaws 260 are constrained so that they cannot expand radially outward. By rotating all of the spoke-like plates 262 together, as seen in FIG. 21B, the compressible jaws 260 are squeezed by reduction in the volume between the plates 262 so that they expand inward. The aggregation of all of the interfaces 264 defines the crimping iris, and compresses any article therewithin. Again, with compressible jaws there are limitations on the magnitude of crimping, and a series of similar crimpers may be used to reduce the size of the article in stages, as described above with respect to FIGS. 20A-20C. Of course, if only a small amount of crimping is necessary, a single crimping mechanism will be suitable.

It should be understood that internal components of the crimping mechanisms described herein may be formed of multiple separate connected parts, or by combining some of these parts in integral members. For example, the six guided jaws 44 seen in FIGS. 11A and 11B are constrained to move with their corresponding guide members 70, and thus these components could be formed as single pieces. To the contrary, certain elements can be broken up into more than one piece, such as the jaws, so as to facilitate manufacturing. This latter instance is illustrated by the crimping mechanism shown in FIGS. 22A-22C.

Figure 22A:
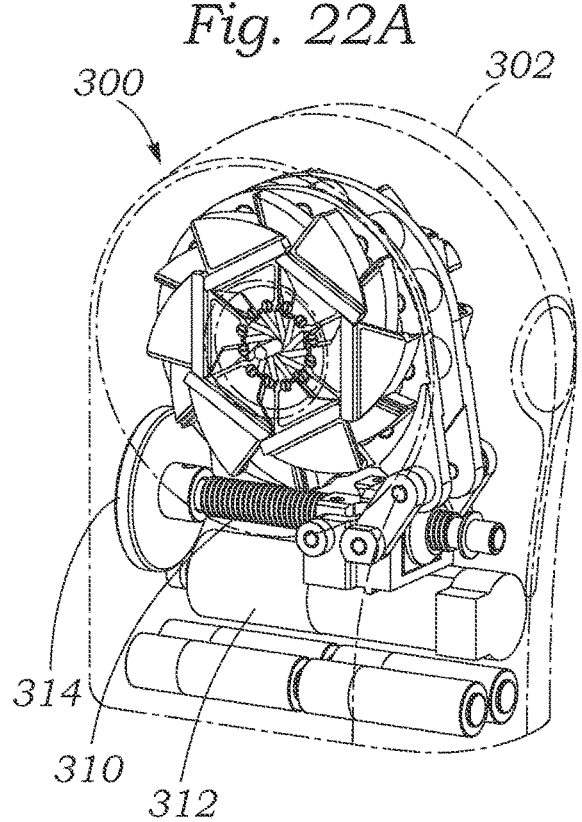
Figure 22B:
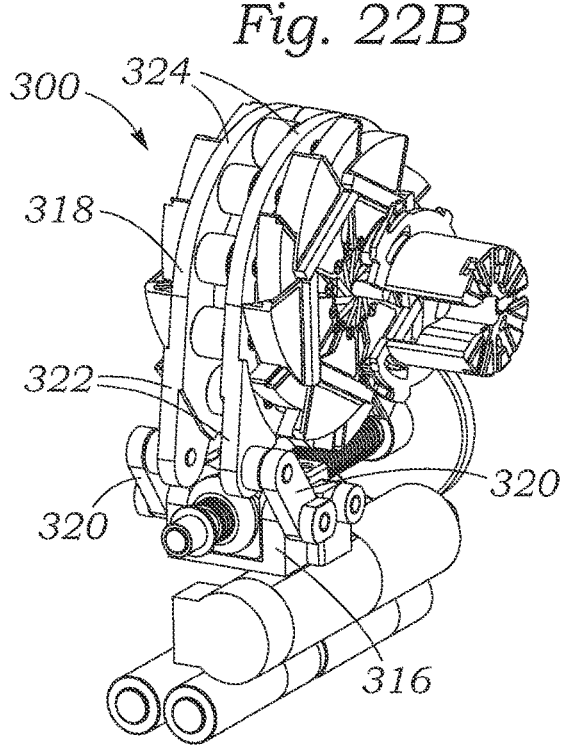
FIG. 22B shows the crimping mechanism from a different perspective and without the outer housing and FIG. 22C shows a number of internal components including crimping jaws exploded.

FIG. 22A is a perspective view of an alternative crimping mechanism 300 having a modified actuating mechanism and an outer housing 302 shown in phantom. FIG. 22B shows the crimping mechanism 300 from a different perspective and without the outer housing 302, and FIG. 22C shows a number of internal components including inner crimping wedges 306 exploded.

The modified actuating mechanism again features a relatively large diameter horizontally oriented lead screw 310 journaled for rotation on either side of the housing 302 and perpendicular to a horizontal crimping axis. A motor 312 in the lower part of the housing 302 is desirably connected via a power transmission (e.g., gears or pulleys 314) to drive the lead screw 310. In contrast with the actuating mechanism described above with respect to FIGS. 2A-2B, rotation of the lead screw 310 causes translation of a carriage assembly 316 which is connected to a cam wheel 318 via a linkage arm 320. That is, the linkage arm 320 is journaled for rotation at opposite ends, one on the carriage assembly 316 and one on an outer lever arm 322 of the cam wheel 318. As with the earlier embodiment, the cam wheel 318 has two spaced apart discs 324 each with a lever arm 322, and there are two of the linkage arms 320, one driving each lever arm. This provides an extremely balanced and robust drive system which prevents binding of the moving jaw components.

This linkage arrangement provides an extended actuation arm that produces higher torque (linear translated to radial) results at the end of crimping process, where the maximal forces are needed. In other words, the stented prosthetic valve is easier to crimp at it larger diameter, and becomes progressively harder as it is constricted. As the carriage assembly 316 reaches the end of the lead screw 310, the linkage arms 320 apply a large amount of torque to the cam wheels 318 relative to each turn of the lead screw.

Figure 22C:
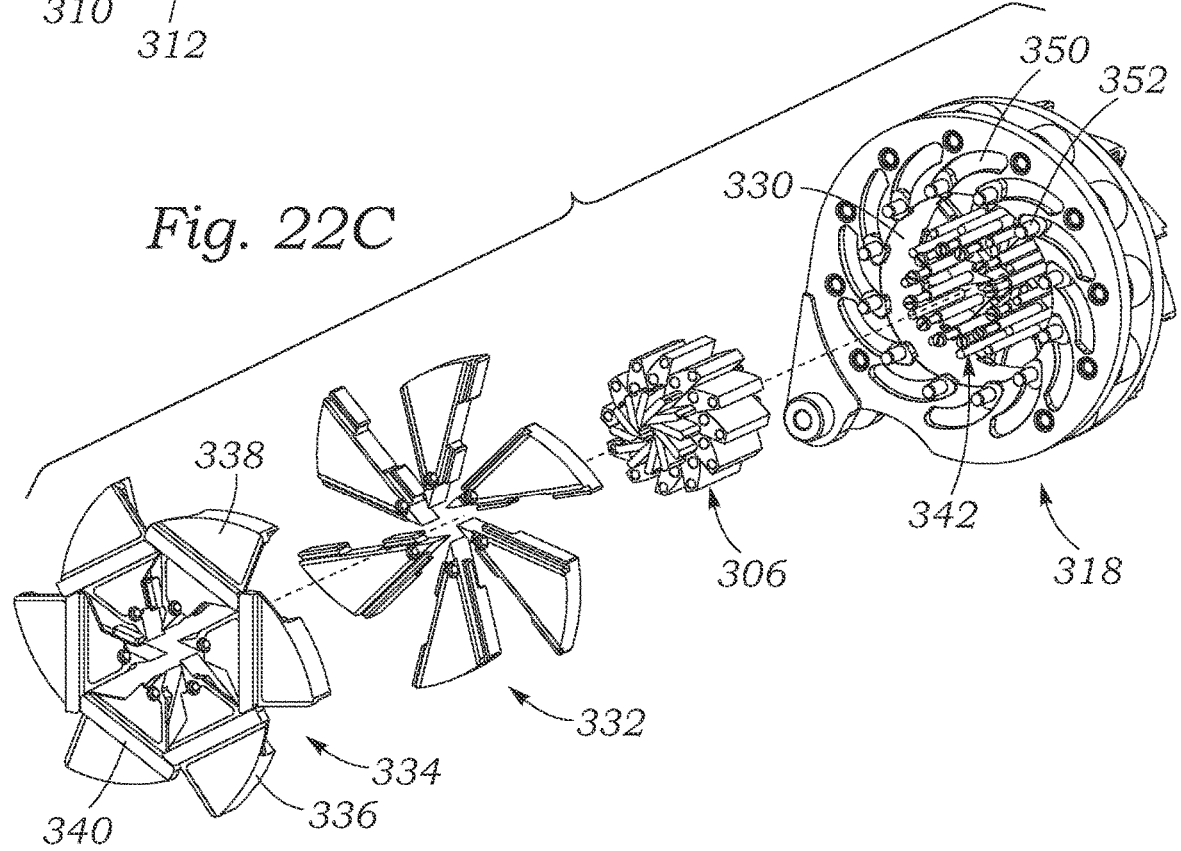

FIG. 22C is an exploded view of the components of the assembly of the cam wheel 318 and jaw mechanism. The crimping wedges 306 are shown arranged in a generally spiral array as they would be held within a central opening 330 in the cam wheel 318. The crimping wedges 306 take the place of the inner crimping wedges 82 of the jaws 44 described above with reference to FIGS. 1A-11E. Flanking each side of the cam wheel 318 is a combination of a set of six generally triangular (pie-shaped) traveler blocks 332 and six guide blocks 334. The guide blocks 334 include essentially two components back-to-back: inner traveler blocks 336 that resemble the traveler blocks 332 and outer guide elements 338 that are similar to the Cartesian guide elements 70 described above. As seen in FIG. 22B, the six traveler blocks 332 and six guide blocks 334 mesh in the same manner as the jaws 44 of FIGS. 1A-11E. The guide elements 338 have linear bars 340 that slide within fixed guide channels (not shown) in the inner faces of the housing 302. Each of the pie-shaped traveler blocks 332, 336 mesh with adjacent blocks in a tongue-in-groove fashion to enable smooth sliding movement therebetween.

A crimping jaw assembly of the crimping wedges 306, six traveler blocks 332 and six guide blocks 334 is formed via a plurality of aligned through bores and bolts 342. As in the earlier version, spiral cam slots 350 in the cam wheel 318 move small cam pins 352 inward as the wheel rotates. The cam pins are held within bores (not shown) on the inner faces of each of the six traveler blocks 332 and six guide blocks 334 so that the blocks are forced along linear paths as constrained by the linear bars 340 sliding within fixed guide channels of the housing 302. This is the same as was described above. The end result is that the inner tips of the crimping wedges 306 translate inward along radial lines to evenly crimp a stented valve therewithin.

Each crimping jaw, per se, includes an assembly of one of the crimping wedges 306 connected at both axial ends to a pair of either the traveler blocks 332 or the guide blocks 334. As can be appreciated, the several components may be manufactured separately of the same or different materials and then secured together across and through the cam wheel 318 via the bolts 342. Preferably, the crimping wedges 306 are formed of a relatively rigid metal, or just inner tips of the crimping wedges 306 may be metal. The sliding pieces may be metal or a hard plastic or resin.

The combination of previously separate parts to form the six guide blocks 334 illustrates the option of using fewer more complicated parts, while the exploded assembly of FIG. 22C shows the option of using more, less complex parts. Ultimately, the choice of which configuration depends on materials, mold cost, engineering difficulty, etc. In a preferred embodiment, an assembly including a wedge 306 plus either two traveler blocks 332 or two guide blocks 334 is formed as one piece, preferably defining twelve jaw assemblies.

Exemplary embodiments of the invention have been described, but the invention is not limited to these embodiments. Various modifications may be made within the scope without departing from the subject matter of the invention read on the appended claims, the description of the invention, and the accompanying drawings.

The invention claimed is:

1. A system, comprising:
   a prosthetic heart valve comprising a self-expandable frame and a plurality of leaflets within the frame, the prosthetic heart valve being radially collapsible and expandable between an expanded configuration having a first diameter and a compressed configuration having a second diameter less than the first diameter; and
   a crimping device for the prosthetic heart valve, the crimping device comprising:
      first and second outer housing members, each housing member having a substantially-circular receiving orifice and a plurality of first slots around an outer perimeter of the respective receiving orifice, the receiving orifices being spaced apart from each other and aligned with respect to a central axis passing through a center of each orifice;
      an actuation wheel, comprising:
         first and second annular disk portions, the annular disk portions being spaced apart from each other and aligned with respect to the central axis, each annular disk portion having a plurality of second slots around an outer perimeter of a central opening of the annular disk portion, the annular disk portions defining a crimping region between the central openings; and
         at least one lever arm, each lever arm extending radially outward from a respective one of the annular disk portions;
      an actuation assembly, comprising:
         a lead screw;
         an internally-threaded carriage engaging with the lead screw and with the at least one lever arm of the actuation wheel; and
      a crimping assembly, comprising:
         a plurality of first and second crimping members arrayed along a circumferential direction of the central openings of the annular disk portions, each crimping member having a first end portion disposed within the crimping region, the first end portions of the crimping members collectively defining a crimping channel within the crimping region, the crimping channel being constructed to receive therein the prosthetic heart valve in the expanded configuration,
         each first crimping member engaging with the housing members via a pair of first engagement portions positioned between the first crimping members and the housing members, one of the pair of first engagement portions being disposed in a respective one of the first slots of the first housing member and the other of the pair being disposed in a respective one of the first slots of the second housing member, wherein the first engagement portions move in the first slots of the housing members between first and second positions along tangential lines that are tangential to central openings, the first engagement portions and the first crimping jaws having cooperating slot and rail structure that permits relatively linear movement therebetween,
         each of the first and second crimping members further engaging with the actuation wheel via a pair of second engagement portions, one of the pair of second engagement portions being disposed in a respective one of the second slots of the first annular disk portion and the other of the pair being disposed in a respective one of the second slots of the second annular disk portion,
      wherein rotation of the lead screw moves the carriage along an axis of the lead screw, which carriage movement rotates the actuation wheel via the engagement with the at least one lever arm of the actuation wheel,
      wherein the rotation of the actuation wheel moves each crimping member via the engagement between the second engagement portions and the respective second slots of the first and second annular disk portions,
      wherein the engagement between the first engagement portions and the respective first slots of the first and second housing members restricts movement of the first crimping members resulting from the rotation of the actuation wheel to translate inward along radial lines toward the central axis and by virtue of the cooperating slot and rail structure displaces the first engagement portions toward the second positions along the first slots of the housing members, and
      wherein the movement of the crimping members changes a diameter of the crimping channel defined by the first end portions, such that the prosthetic heart valve is radially compressed to the compressed configuration.

2. The system of claim 1, wherein, for each first crimping member:
   one or both of the first engagement portions are part of a separate element coupled to the first crimping member,
   said one or both of the first engagement portions extend in a direction parallel to the central axis, and
   the separate element is coupled thereto via a portion of the separate element inserted into a receiving portion of the first crimping member.

3. The system of claim 1, wherein, for each of the first and second crimping members, one or both of the second engagement portions are part of a separate element coupled to the respective crimping member.

4. The system of claim 1, wherein, for each first crimping member, the first engagement portions and the second engagement portions are part of or coupled to the first crimping member.

5. The system of claim 1, wherein each crimping member has an inner surface and an outer surface, and the outer surface contacts and is shaped to match the inner surface of an adjacent one of the crimping members.

6. The system of claim 1, wherein:
   each second slot of the first and second annular disk portions has an arcuate shape with one end of the second slot being closer along radial direction to the respective central opening than an opposite end of the second slot, and each first slot of the first and second housing members has a substantially linear shape with one end of the first slot being closer along the radial direction to the respective receiving orifice than an opposite end of the first slot.

7. The system of claim 1, wherein, for each first crimping member, at least one of the first and second engagement portions comprises a bolt that extends through the first crimping member in a direction parallel to the central axis.

8. The system of claim 1, wherein the carriage includes at least one shaft stub that engages with a corresponding opening in the at least one lever arm.

9. The system of claim 1, wherein the lead screw extends substantially parallel to a direction perpendicular to the central axis, and the actuation assembly comprises an actuation member coupled to an end of the lead screw, the actuation member being disposed external to the first and second housing members and being constructed for manual rotation of the lead screw.

10. The system of claim 1, wherein:
a difference between the first diameter of the expanded configuration and the second diameter of the compressed configuration is at least 14 mm; or
the first diameter of expanded configuration is at least 3.3 times greater than the second diameter of the compressed configuration.

11. A system, comprising: a prosthetic heart valve comprising a self-expandable frame and a plurality of leaflets within the frame, the prosthetic heart valve being radially collapsible and expandable between an expanded configuration having a first diameter and a compressed configuration having a second diameter less than the first diameter; and a crimping device for the prosthetic heart valve, the crimping device comprising: first and second outer housing members, each housing member having a substantially-circular receiving orifice and a plurality of first slots extending outwardly from around an outer perimeter of the respective receiving orifice in tangential lines; an actuation wheel comprising first and second annular disk portions, the annular disk portions being spaced apart from each other and aligned with respect to a central axis, each annular disk portion having a plurality of second slots around an outer perimeter of a central opening of the annular disk portion; an actuation assembly coupled to the actuation wheel and constructed to rotate the actuation wheel about the central axis, wherein the actuation assembly comprises a screw operatively coupled to the actuation wheel; and a c rimping assembly coupled to the actuation wheel and comprising a plurality of crimping members arranged along a circumferential direction of the central openings of the annular disk portions, each crimping member having a first end portion closest to the central axis, the first end portions of the crimping members collectively defining at least part of a crimping channel, the crimping channel being constructed to receive therein the prosthetic heart valve in the expanded configuration, wherein at least some of the crimping members have first engagement portions disposed in respective first slots of the first and second housing members, wherein the first engagement portions are positioned between the crimping members and the housing members, wherein the first engagement portions move in the first slots of the first and second housing members between first and second positions along tangential lines that are tangential to central openings, the first engagement portions and the crimping jaws having cooperating slot and rail structure that permits relatively linear movement therebetween, wherein rotation of the screw produces rotation of the actuation wheel, which in turn moves each crimping member via second engagement portions disposed in respective second slots of the first and second annular disk portions, wherein movement of each crimping member is constrained by first engagement portions disposed in respective first slots of the first and second housing members to translate inward along radial lines toward the central axis by virtue of the cooperating slot and rail, and wherein the inward movement of the crimping members changes a diameter of the crimping channel, such that the prosthetic heart valve is radially compressed to the compressed configuration.

12. The system of claim 11, wherein the first engagement portions and/or the second engagement portions are part of or coupled to the crimping members.

13. The system of claim 11, wherein the actuation assembly comprises a manually-actuatable member coupled to an end of the screw and disposed external to the first and second housing members, and the manually-actuatable member is configured to be manually rotated by a user to rotate the screw.

14. The system of claim 11, wherein:
each second slot has an arcuate shape with one end thereof being closer to the central axis than an opposite end thereof, and
each first slot has a substantially linear shape with one end thereof being closer to the central axis than an opposite end thereof, each first slot extending through a thickness of the respective one of the first and second housing members.

15. The system of claim 11, wherein:
a difference between the first diameter of the expanded configuration and the second diameter of the compressed configuration is at least 14 mm; or
the first diameter of expanded configuration is at least 3.3 times greater than the second diameter of the compressed configuration.

16. A system, comprising: a prosthetic heart valve comprising a self-expandable frame and a plurality of leaflets within the frame, the prosthetic heart valve being radially collapsible and expandable between an expanded configuration having a first diameter and a compressed configuration having a second diameter less than the first diameter, the prosthetic heart valve having a first central axis; a catheter for delivery of the prosthetic heart valve in the compressed configuration to an implantation site, the catheter extending in a direction substantially parallel to the first central axis; and a crimping device for the prosthetic heart valve, the crimping device comprising: first and second outer housing members, each housing member having a substantially-circular receiving orifice and a plurality of first slots extending outwardly from around an outer perimeter of the respective receiving orifice in tangential lines; an actuation wheel comprising first and second annular disk portions, the annular disk portions being spaced apart from each other and aligned with respect to a second central axis, each annular disk portion having a plurality of second slots around an outer perimeter of a central opening of the annular disk portion, each annular disk portion further having a flange that protrudes radially outward from an outer circumference of the annular disk portion; an actuation assembly coupled to the actuation wheel and constructed to rotate the actuation wheel about the second central axis, wherein the actuation assembly comprises a screw and a carriage coupled to the flanges of the annular disk portions, the screw extending through the carriage in a region between the flanges such that threads of the screw engage with corresponding threads of the carriage; and a crimping assembly coupled to the actuation wheel and comprising a plurality of crimping members arranged along a circumferential direction of the central openings of the annular disk portions, each crimping member having a first end portion closest to the second central axis, the first end portions of the crimping members collectively defining at least part of a crimping channel, the crimping channel being constructed to receive therein the prosthetic heart valve in the expanded configuration with the first central axis being substantially aligned with the second central axis, wherein at least some of the crimping members have first engagement portions disposed in respective first slots of the first and second housing members, wherein the first engagement portions are positioned between the crimping members and the housing members, wherein the first engagement portions move in the first slots of the first and second housing members between first and second positions along tangential lines that are tangential to central openings, the first engagement portions and the crimping jaws having cooperating slot and rail structure that permits relatively linear movement therebetween, wherein rotation of the screw produces rotation of the actuation wheel via the carriage and the flanges of the annular disk portions, which in turn moves each crimping member via second engagement portions disposed in respective second slots of the first and second annular disk portions, wherein movement of each crimping member is constrained by first engagement portions disposed in respective first slots of the first and second housing members to translate inward along radial lines toward the central axis by virtue of the cooperating slot and rail, and wherein the inward movement of the crimping members changes a diameter of the crimping channel, such that the prosthetic heart valve is radially compressed to the compressed configuration.

17. The system of claim 16, wherein the actuation assembly comprises a manually-actuatable member coupled to an end of the screw and disposed external to the first and second housing members, and the manually-actuatable member is configured to be manually rotated by a user to rotate the screw.

18. The system of claim 16, wherein the catheter has a sheath constructed for insertion therein of the prosthetic heart valve in the compressed configuration.

19. The system of claim 16, wherein:
a difference between the first diameter of the expanded configuration and the second diameter of the compressed configuration is at least 14 mm; or
the first diameter of expanded configuration is at least 3.3 times greater than the second diameter of the compressed configuration.

\* \* \* \* \*